United States Patent [19]

Watanabe et al.

[11] 4,438,107

[45] Mar. 20, 1984

[54] AMINOGLYCOSIDES AND USE THEREOF

[75] Inventors: Isamu Watanabe, Higashimurayama; Takashi Yamaguchi, Tokyo; Kazuhiro Kamiya; Toshihito Mori, both of Higashimurayama; Hamao Umezawa; Sumio Umezawa, both of Tokyo; Tsutomu Tsuchiya, Yokohama, all of Japan

[73] Assignees: Kowa Company, Ltd., Aichi; Zaidan Hojin Biseibutsu Kagaku Kenkyu Kai, Tokyo, both of Japan

[21] Appl. No.: 402,812

[22] Filed: Jul. 28, 1982

[30] Foreign Application Priority Data

Jul. 29, 1981 [JP] Japan ................................ 56-117856

[51] Int. Cl.[3] ........................ A61K 31/70; C08B 37/00

[52] U.S. Cl. ................................... 424/180; 536/16.1; 536/16.8; 536/17.9

[58] Field of Search .................... 536/16.1, 16.8, 17.9; 424/180

[56] References Cited

U.S. PATENT DOCUMENTS

| | | | |
|---|---|---|---|
| 4,206,206 | 6/1980 | Mori et al. | 536/16.8 |
| 4,255,421 | 3/1981 | Watanabe et al. | 536/17.9 |

*Primary Examiner*—Alan Siegel

*Attorney, Agent, or Firm*—Wenderoth, Lind & Ponack

[57] ABSTRACT

An aminoglycoside compound of the following formula

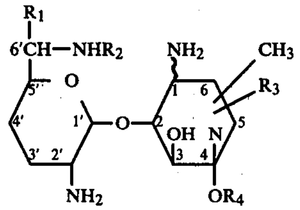

(I)

wherein one of $R_1$ and $R_2$ represents a hydrogen atom and the other, a methyl group, $R_3$ represents a hydrogen atom or an amino acyl group having 2 to 5 carbon atoms, $R_4$ represents a lower alkyl group substituted by one or two substituents selected from the class consisting of hydroxy and amino groups, or a hexopyranosyl group whose hydroxy groups may be substituted by amino groups, and a pharmaceutically acceptable acid addition salt thereof; and an antibiotic composition comprising said compound and its pharmaceutically acceptable acid addition salt.

4 Claims, No Drawings

AMINOGLYCOSIDES AND USE THEREOF

This invention relates to novel aminoglycosides useful as antibiotics. The invention also pertains to a process for production thereof, and use thereof.

More specifically, this invention relates to a compound of the following formula

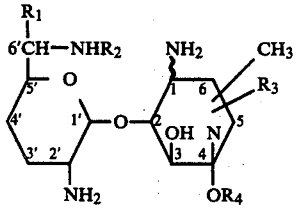

(I)

wherein one of $R_1$ and $R_2$ represents a hydrogen atom and the other, a methyl group, $R_3$ represents a hydrogen atom or an amino acyl group having 2 to 5 carbon atoms, $R_4$ represents a lower alkyl group substituted by one or two substituents selected from the class consisting of hydroxyl and amino groups, or a hexopyranosyl group whose hydroxy groups may be substituted by amino groups, and a pharmaceutically acceptable acid addition salt thereof.

The invention also pertains to a process for producing the compound of formula (I) and a pharmaceutically acceptable acid addition salt thereof, and an antibiotic composition comprising said compound of formula (I) and its pharmaceutically acceptable acid addition salt.

Antibiotic KA-6606 substances are known which can be obtained by cultivating antibiotic KA-6606-producing strains belonging to the genus Saccharo-polyspora, such as *Saccharopolyspora hirsuta* KC-6606 strain (known and available as FERM-P No. 3912 in Fermentation Research Institute, Agency of Industrial Science & Technology, Japan; ATCC 20501 in American Type Culture Collection; DSM No. 1238 in German Collection of Microorganisms), [see U.S. Pat. Nos. 4,206,206 and 4,255,421; German OLS 2813021 and 2942194; and Japanese Laid-Open Patent Publication Nos. 127401/1978, 66603/1979, 11497/1980, 21383/1982 and 109798/1982]. Also known are antibiotic KA-7038 substances which are obtained by cultivating antibiotic KA-7038-producing strains belonging to the genus Streptomyces, such as Streptomyces sp. KC-7038 strain (known and available as FERM-P No. 4388; ATCC 31530; DMS No. 1594 1771)) [see U.S. Pat. Nos. 4,312,858 and 4,255,421; German OLS No. 2928373 and 2942194, and German Laid-Open Patent Publication Nos. 141701/1979, 11541/1980 and 162795/1980].

The above-cited U.S. Pat. No. 4,255,421 (German OLS 2942194 and Japanese Laid-Open Pat. Publication Nos. 55198/1980 and 2997/1981) discloses 5-de-O-methyl derivatives of the following formula (III)' which are derived from antibiotics KA-6606 I to IV, and VI and antibiotics KA-7038 I and III represented by the following formula (II); processes for production thereof; and antibiotic compositions comprising such 5-de-O-methyl derivatives.

| Antibiotics | $R_1$ | $R_2$ | Y | Orientation of the amino group at 1-position to the sugar moiety at 2-position |
|---|---|---|---|---|
| 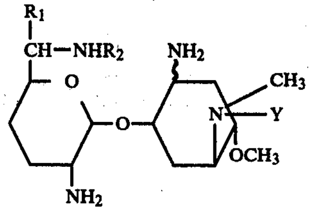 | | | | (II) |
| KA-6606 | | | | |
| I | $CH_3$ | H | $COCH_2NH_2$ | cis |
| II | $CH_3$ | H | H | cis |
| III | $CH_3$ | H | $COCH_2NHCONH_2$ | cis |
| IV | $CH_3$ | H | $COCH_2NHCHO$ | cis |
| VI | $CH_3$ | H | H | trans |
| KA-7038 | | | | |
| I | H | $CH_3$ | $COCH_2NH_2$ | trans |
| III | H | $CH_3$ | H | trans |
| 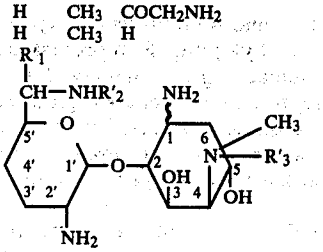 | | | | (III)' |

wherein $R_1'$ and $R_2'$ are identical or different and each represents a hydrogen atom or a methyl group, $R_3'$ represents a hydrogen atom or an unsubstituted or substituted aminoacyl group having 2 to 4 carbon atoms in the acyl moiety, the substituent being selected from the group consisting of hydroxy, formyl, and carbamoyl, and when all of $R_1'$, $R_2'$ and $R_3'$ are hydrogen atoms, the methylamino group at the 4-position is not oriented trans to the hydroxyl groups at the 3- and 5-positions; or a pharmaceutically acceptable acid addition salt thereof.

The present inventors have made investigations about derivatives from the aforesaid known aminoglycosides. These investigations have led to the discovery that compounds of formula (I) given hereinabove derived from compounds of the following formula (III)

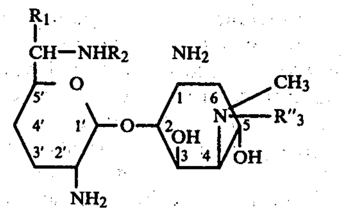

(III)

wherein one of $R_1$ and $R_2$ represents a hydrogen atom and the other represents a methyl group, and $R_3''$ represents a hydrogen atom or an aminoacyl group having 2 to 5 carbon atoms, which are embraced by the compounds of formula (III)', given above and in which the OH group at the 5-position has been converted to the group $-OR_4$ wherein $R_4$ is as defined with regard to formula (I) can be synthesized, and that the compounds of formula (I) are novel amino-glycosides having excellent antibiotic activity.

It is the object of this invention therefore to provide the novel aminoglycosides of formula (I).

Another object of this invention is to provide a process for producing the compounds of formula (I) and their use.

The above and other objects of this invention along with its advantages will become more apparent from the following description.

The novel aminoglycosides of this invention are expressed by the above formula (I) and also include their pharmaceutically acceptable acid addition salts.

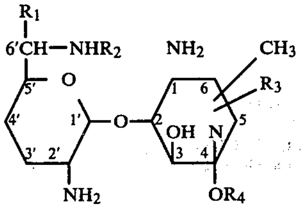

(I)

wherein one of $R_1$ and $R_2$ represents a hydrogen atom and the other, a methyl group, $R_3$ represents a hydrogen atom or an aminoacyl group having 2 to 5 carbon atoms, and $R_4$ represents a lower alkyl group substituted by one or two substituents selected from the class consisting of hydroxy and amino groups, or a hexopyranosyl group whose hydroxy groups may be substituted by amino groups.

Examples of the $C_2$–$C_5$ aminoacyl group for $R_3$ in formula (I) include glycyl, alanyl, valyl and sarcosyl groups. Examples of the lower alkyl group, preferably $C_2$–$C_6$ alkyl group, for $R_4$ substituted by one or two substituents selected from the class consisting of hydroxy and amino groups are $-CH_2CH_2OH$,
$-CH_2CH_2NH_2$, $-CH_2CH(OH)CH_2OH$, $-CH_2CH(OH)CH_2NH_2$, $-CH_2CH(OH)CH_2CH_2NH_2$, 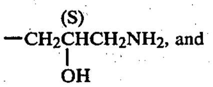, and

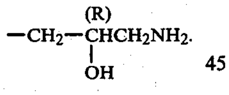.

Furthermore, examples of the hexopyranosyl group for $R_4$ whose hydroxy group may be substituted by an amino group are glucopyranosyl, mannopyranosyl, galactopyranosyl, idopyranosyl and gulopyranosyl groups whose hydroxy groups may be replaced by amino groups. The steric configuration at the 1-position may be α or β. One to three of the hydroxyl groups of these sugar moiety may be substituted by amino groups. A glucopyranosyl group or a glucopyranosyl group having amino at the 3-position is a preferred example.

The compound of formula (I) of this invention can be produced, for example, by etherification involving the introduction of the group $R_4$ into the 5-position OH group of the compound of formula (III). The starting compound of formula (III) may be obtained by 5-de-O-methylating the compound of formula (II) given above by known methods, such as that described in U.S. Pat. No. 4,255,421. Specifically, this can be effected by treating the compound of formula (II) with a strong acid, for example a mineral acid such as hydrobromic acid, hydriodic acid or hydrofluoric acid, or a Lewis acid such as boron trichloride, boron tribromide or boron trifluoride. Or it can be effected by the action of an alkali metal and an amine on the compound of formula (II).

When a compound of formula (II) in which Y is an acyl group or a substituted acyl group is used, elimination of the acyl group takes place simultaneously with 5-de-O-methylation to give a compound of formula (III)' in which $R_3'$ is a hydrogen atom, or a compound of formula (III) in which $R_3''$ is a hydrogen atom. As required, the compound may be acylated to introduce a $C_2$–$C_5$ aminoacyl group.

Etherification reaction involving the introduction of the group $R_4$ into the OH group at the 5-position of the starting compound of formula (III) can be carried out by various procedures, examples of which are shown in (a) to (d) below.

(a) The compound of formula (III) is reacted with a compound of the following formula $$X—R_4 \qquad (IV)$$

wherein X represents a halogen atom, a substituted sulfonyloxy group, or a substituted sulfuric acid group, and $R_4$ is as defined in formula (I), preferably in the presence of a basic catalyst.

Examples of the substituted sulfonyloxy group are o-nitrobenezene sulfonyloxy, methanesulfonyloxy, p-toluenesulfonyloxy, and trifluoromethanesulfonyloxy groups. Examples of the substituted sulfuric acid group include chlorosulfonyloxy and alkylsulfate groups such as methyl sulfate group.

Examples of the basic catalyst include alkali metal hydroxides, alkali metal hydrides, alkali metals, mercuric cyanide, mercuric halides, silver perchlorate, silver p-toluenesulfonate, silver carbonate, γ-collidine, and mixtures of these. The amino and hydroxyl groups in $R_4$ are preferably protected. The same can be said with regard to amino groups and hydroxyl groups other than the 5-position OH in the compound of formula (III). Methods of introducing a protective group are known per se. and any known method can be used in this invention. Some specific examples will be given hereinbelow. The same applies to the following procedures (b) to (d).

The reaction is carried out by using 1 to 10 moles, per mole of the compound of formula (III), of the compound of formula (IV) in a solvent such as benzene, dioxane, dichloromethane or dimethylformamide at a temperature of −10° C. to 100° C. in the presence of the basic catalyst.

One example of the procedure (a) is schematically shown below. The compound of formula (III) is represented by (III)—OH, and it is supposed that a glucopyrasonyl group is to be introduced as $R_4$.

(III)—OH + 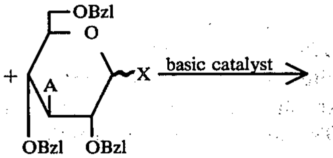

wherein

Bzl = 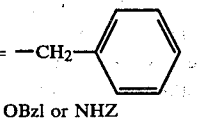

A = OBzl or NHZ

-continued

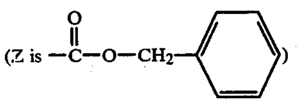

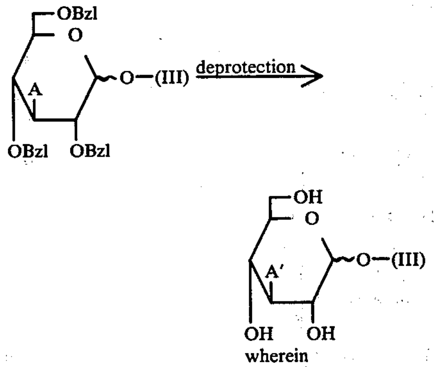

wherein
A' = OH or $NH_2$
Compound of formula (I)

(b) The compound of formula (III) is reacted with a compund of the following formula $$X—R_4' \quad (V)$$

wherein X is as defined with regard to formula (IV), $R_4'$ represents an alkenyl group, preferably a $C_2$–$C_6$ alkenyl group such as a vinyl, allyl, propenyl or butenyl group, or an alkyl group, preferably a $C_2$–$C_6$ alkyl group, having an epoxy group,
and then one or two substituents selected from the class consisting of hydroxy and amino groups are introduced into the alkenyl or arlkyl group.

The introduction of the substituents can be effected by a suitable combination of unit reactions known per se such as oxidation, reduction, epoxy ring opening, ozonolysis addition, elimination, and substitution reaction. Specific examples include a combination of ozonolysis, esterification, azido introduction (substitution reaction), and then reduction; a combination of oxidation (epoxidation), ring opening by an azide ion, and then reduction; a combination of oxidation (epoxidation), ring opening by a cyanide ion, and then reduction; a combination of oxidation (epoxidation) and then ring opening by an acid; and a combination of ring opening by an acid, esterification, azido introduction (substitution), and then reduction.

The reaction of the compound of formula (III) with the compound of formula (V) in which $R_4'$ is an alkenyl group is desirably carried out in the presence of a base which is the same as those exemplified with regard to procedure (a).

This reaction can be carried out in the same way as in procedure (a).

The reaction of the resulting reaction product to convert the alkenyl group in it into an alkyl group having one or two substituents selected from the class consisting of hydroxy group and amino group by a suitable combination of the above-mentioned unit reactions can be performed, for example, in the following manner.

Ozonolysis can be carried out, for example, by blowing ozone gas at −80° C. to 0° C. in a solvent such as dichloromethane, chloroform, ethyl acetate and ethanol. The resulting ozonide can be converted to an aldehyde or ketone by hydrogenating it with zinc, sodium iodide or palladium. Or the ozonide may be converted to an alcohol by reduction with sodium borohydride, for example.

Esterification can be carried out by using an esterification reagent such as an acid anhydride or an acid halide in an amount of 1 to 5 moles per mole of the compound to be esterified in an inert solvent such as benzene or chloroform in the presence of a base such as pyridine, collidine or triethylamine, or using pyridine as a solvent at −40° C. to 80° C. The reaction is completed in several minutes to several hours.

Azido introduction (substitution) can be carried out, for example, by adding 3 to 10 moles of an alkali azide in a solvent such as dimethylformamide or dioxane, and effecting the reaction at 50° to 120° C. for 1 to 20 hours.

Oxidation (epoxidation) can be carried out, for example, by adding 1 to 10 moles, per mole of the compound to be reacted, of a peracid such as perbenzoic acid, m-chloroperbenzoic acid, performic acid, peracetic acid or trifluoroperacetic acid in an inert solvent such as methylene chloride or chloroform, and carrying out the reaction at 0° to 80° C. for 1 to 20 hours.

Ring opening by an azide ion may be carried out in quite the same way as in the aforesaid azido substitution.

Ring opening by a cyanide ion may be carried out, for example, by adding 3 to 10 moles, per mole of the compound to be reacted, of an alkali cyanide in a solvent such as dimethylformamide or dioxane, and effecting the reaction at 50° to 120° C.

Ring opening by an acid can be carried out, for example, by adding an acid such as sulfuric acid or hydrochloric acid in a solvent such as water or water-containing dioxane or dimethylformamide, and effecting the reaction at 0° to 50° C. for 0.1 to 20 hours.

Reduction can be carried out, for example, by hydrogenating the compound to be reacted at a hydrogen pressure of 1 to 5 atmospheres and a reaction temperature of 0° to 100° C. in water, methanol, dioxane, or acetic acid or a mixture thereof, preferably in the presence of an acid such as hydrochloric acid or acetic acid, using palladium, platinum, rhodium, Raney nickel, etc. as a catalyst.

The reaction of the compound of formula (III) with a compound of formula (V) in which $R_4'$ is an alkyl group having an epoxy group is carried out at −10° C. to 100° C. for 0.5 to 20 hours in a solvent such as dimethylformamide or dioxane in the presence of a basic catalyst such as sodium hydride, an alkali hydroxide.

The reaction of the resulting reaction product to convert the alkyl group containing an epoxy group into an alkyl group having hydroxy and amino can be carried out, for example, by a combination of ring opening by an acid, esterification, azido introduction (substitution) and then reduction under the same conditions as described above, or a combination of ring opening by an azide ion or a cyanide ion and then reduction under the same conditions as described hereinabove.

Several examples of procedure (b) are schematically shown below. The compound of formula (III) is represented by (III)—OH, and it is supposed that a lower alkyl group substituted by one or two substituents selected from the class consisting of hydroxy and amino groups is to be introduced.

Several examples of $R'_4$ = alkenyl (allyl)

-continued
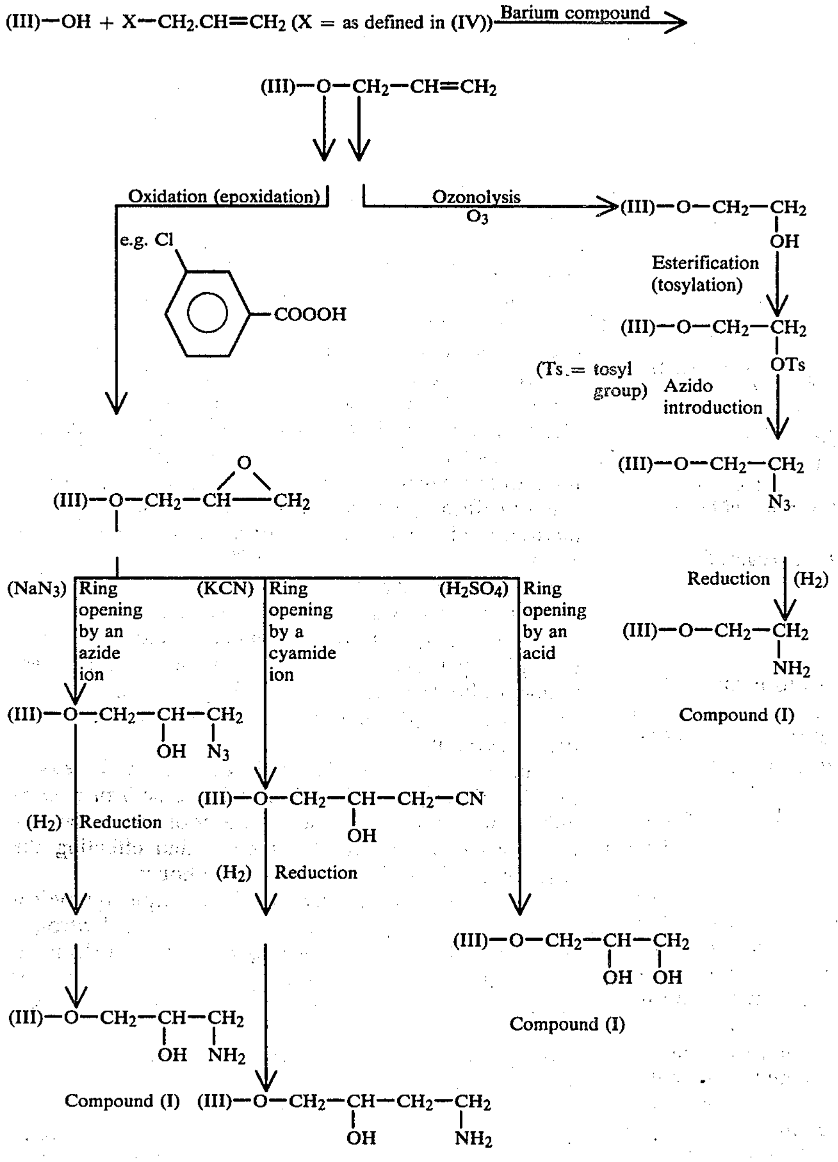
Compound (I)
Compound (I)
Compound (I)
Compound (I)
Example of R'4 = alkyl group having an epoxy group
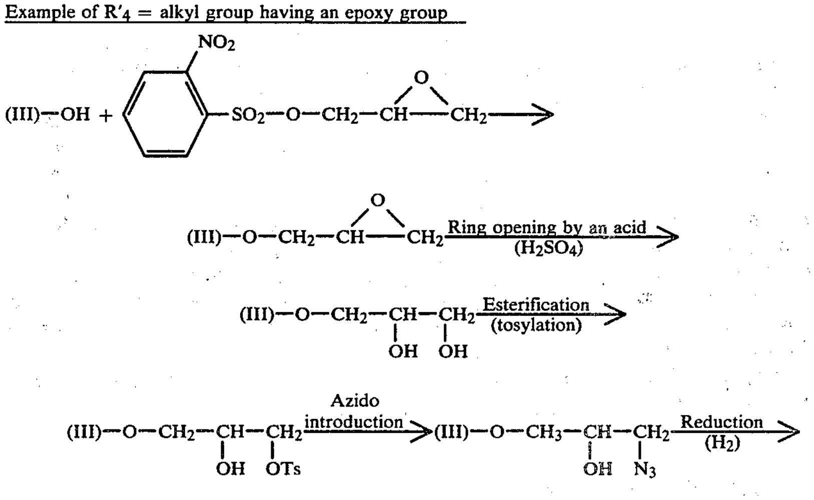

-continued

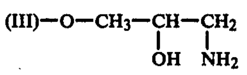

Compound (I)

(c) The compound of formula (III) is reacted with a compound of the following formula $$R_4''4{=}N_{\oplus}{=}N_{\ominus} \quad \text{(VI)}$$

wherein $R_4''$ represents an alkylidene group having 2 to 6 carbon atoms, in the presence of a Lewis acid.

Examples of the Lewis acid used in this reaction are boron trifluoride etherate and aluminum chloride.

The reaction is carried out by adding the diazo compound in the presence of the Lewis acid in a solvent such as benzene or dichloromethane at −80° to 50° C., and effecting the reaction for 0.1 to 5 hours.

(d) The compound of formula (III) is reacted with an unsaturated hydrocarbon such as a $C_2$–$C_6$ unsaturated hydrocarbon having a double or triple bond in the presence of a catalyst.

An acid catalyst and a basic catalyst can be used as the catalyst. Examples include sulfuric acid, toluenesulfonic acid, Lewis acids such as boron trifluoride, basic catalysts such as sodium alkoxides.

The reaction is carried out, for example, in the absence or presence of a solvent such as chloroform, ethanol or dimethylformamide in the presence of the aforesaid catalyst at 0° C. to 150° C. for 0.5 to 20 hours.

In the above procedures (a) to (d) for producing the novel aminoglycosides of formula (I) in accordance with this invention, it is preferred that the amino groups, and the hydroxyl group at the 3-position of the compound of formula (III) and also those of the compound of formula (IV) be protected before performing the etherification of the hydroxyl group at the 5-position of the compound of formula (III). Methods of protecting the amino groups and hydroxyl groups and eliminating the protective groups are known per se, and any known method can be used in the present invention. Several examples are given below.

Known protective groups for an amino group which have heretofore been utilized in peptide synthesis can be used as protective groups for the amino group. For example, protective groups of the following formula

wherein A represents an alkyl, cycloalkyl, aryl or aralkyl group, are preferred. Examples of such protective groups include alkyloxycarbonyl groups such as ethyloxycarbonyl, tertiary butyloxycarbonyl, tertiary amyloxycarbonyl groups; cycloalkyloxycarbonyl groups such as a cyclohexyloxycarbonyl group; aryloxycarbonyl groups such as a phenoxycarbonyl group; and aralkyloxycarbonyl groups such as benzyloxycarbonyl and p-methoxybenzyloxycarbonyl groups.

Introduction of a protective group can be carried out by known methods. For example, this is preferably effected by the action of a carboxylic acid of the formula $$A{-}OCOOH \quad \text{(VII)}$$

wherein A is as defined, or its reactive derivative upon the compound of formula (III). Examples of the reactive derivatives of the carboxylic acid include and halides, acid azides, acid anhydrides, and active esters. Thereafter, only the hydroxyl group at the 3-position of the compound of formula (III) is selectively protected. Since an amino group exists at the 4-position adjacent to the hydroxyl group at the 3-position of the compound of formula (III), a cyclic carbamate is first formed by utilizing the amino group at the 4-position, whereby the hydroxyl group at the 3-position can be protected easily together with the amino group at the 4-position. The cyclic carbamate can be formed by, for example, reacting the compound of formula (III) which is tetra-N-protected with an alkali, preferably in a solvent. Examples of the alkali used are sodium hydride, barium hydroxide, sodium hydroxide, and calcium hydroxide. Examples of the solvent used are dimethylformamide, dioxane, tetrahydrofuran, water, and mixtures of these.

When the methylamino group at the 4-position of a compound of formula (I) in which $R_3$ is a hydrogen atom is acylated, a compound of formula (I) in which $R_3$ in an acyl group can be obtained. Acylation is carried out after liberating the methylamino group at the 4-position. Specifically, the methylamino group at the 4-position can be easily freed by hydrolyzing the cyclic carbamate between 3- and 4-positions. The hydrolysis can be carried out by usual acid or alkaline hydrolysis.

When in the above etherification reaction, the protective groups are simultaneously eliminated or the protective groups are eliminated in advance, the amino groups at the 1-, 2'- and 6'-positions are first protected. This protecting reaction can be carried out in the same way as in the protection of the amino groups in the compound of formula (III) described above. Since at this time the methylamino group at the 4-position is simultaneously protected, it is necessary to free the methylamino group at the 4-position to be acylated. For this purpose, a cyclic carbamate is formed between the hydroxyl group at the 3-position and the methylamino group at the 4-position, and then hydrolyzed. As a result, the methylamino group at the 4-position alone can be easily freed. The hydrolysis can be carried out in accordance with usual acid or alkaline hydrolysis.

The action of an alkali upon the tetra-N-protected compound in a water-containing solvent can directly induce the selective freeing of the methylamino group at the 4-position.

When in the protection of the amino groups of the compound of formula (III) or (I) in which $R_3$ is H, an active ester, such as a substituted phenyl ester, N-oxysuccinimide ester or N-oxyphthalimide ester, especially an active ester represented by the general formula

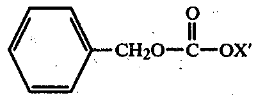

wherein X' represents a phenyl, succinimidyl or phthalimidyl group which may be substituted,
is used as the reactive derivative of the carboxylic acid of formula (VII), the amino groups at the 1-, 2'- and 6'-positions can be selectively protected. Favorable results can be obtained by performing this reaction in the presence of a metallic compound such as nickel acetate, cobalt acetate or copper acetate.

When the methylamino group at the 4-position of the resulting compound of formula (I) ($R_3$=H) in which the amino groups at the 1-, 2'- and 6'-positions are protected is acylated, a compound of formula (I) in which the amino groups are protected can be obtained.

Preferred acylating agents are amino acids such as glycine, alanine, valine, and sarcosine. Acylation with amino acids can be carried out in accordance with an ordinary peptide synthesizing method, and an N-protected amino acid or its reactive derivative is used as an acylating agent. Protective groups for the amino group of the amino acid may be the same protective groups as mentioned above. They may be the same as, or different from, the protective groups of the compound of formula (I) ($R_3$=H). In order to perform the elimination reaction in the next step easily, it is preferred to use the same protective groups. The amino groups may be substituted by lower alkyl groups, carbamoyl groups, formyl groups, etc. The acid-reactive derivatives of the amino acids may be the same as the reactive derivatives of the carboxylic acid of formula (VII).

The compound of formula (I) in free form can be obtained by eliminating the protective groups from the resulting compound of formula (I) ($R_3$=H or aryl) in which the amino groups and/or hydroxyl group are protected. Usual methods can be applied to the elimination of the protective groups for the amino groups and the hydroxyl group, but catalytic reduction and acid hydrolysis are preferred. Palladium, platinum, Raney nickel, rhodium, ruthenium, and nickel are examples of the catalyst used for catalytic reduction. As a solvent, there can be used water, methanol, ethanol, dioxane, tetrahydrofuran, acetic acid, or a mixture thereof. This reaction can be carried out, for example, at a hydrogen pressure of about 1 to about 5 atmospheres and a reaction temperature of about 0 to about 100° C. for about 0.1 to about 10 hours.

The desired compound of formula (I), with or without the protection of its amino groups and/or hydroxyl group, can be isolated and purified in a customary manner. Column chromatography is especially preferred. A cation exchange resin, such as CM-Sephadex, Amberlite, IRC-50, IRC-84 and CG-50 and carboxymethyl cellulose, is preferably used as an adsorbent. Elution can be carried out by a concentration gradient method or a concentration stepwise method by using an aqueous alkaline solution, such as aqueous ammonia or an aqueous solution of ammonium formate, as a developing solvent. Active fractions were collected from the eluate, and lyophilized to give the desired compound in pure form.

The compound of formula (I) may be converted to its pharmaceutically acceptable acid addition salt in a customary manner by using inorganic acids such as sulfuric acid, hydrochloric acid, hydrobromic acid, hydriodic acid, phosphoric acid, carbonic acid and nitric acid, or organic acids such as acetic acid, fumaric acid, malic acid, critic acid, mandelic acid and succinic acid.

The compound of formula (I) and its pharmaceutically acceptable acid addition salt have good antibiotic activity, and are useful in the field of medicines for man and other animals, and also as intermediates for the synthesis of derivatives.

Thus, the present invention can provide an antibiotic composition comprising the novel compound of formua (I).

Specifically, according to this invention, there is provided an antibiotic composition composed of (i) an antibiotically effective amount of a compound having the following formula

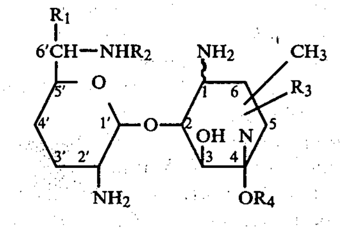

(I)

wherein one of $R_1$ and $R_2$ represents a hydrogen atom and the other, a methyl group, $R_3$ represents a hydrogen atom or an amino acyl group having 2 to 5 carbon atoms, $R_4$ represents a lower alkyl group substituted by one or two substituents selected from the class consisting of hydroxy and amino groups, or a hexopyranosyl group whose hydroxy group may be substituted by an amino group,
or a pharmaceutically acceptable acid addition salt thereof, and (ii) a pharmaceutically acceptable diluent or carrier.

The amount of the compound (I) is, for example, about 0.01 to about 99.5% by weight, based on the weight of the composition.

The antibiotic composition of this invention may be in any of the dosage forms usually employed, but injecting preparations and capsules are especially preferred.

Preferably, like known water-soluble basic antibiotics, an injectable is prepared by filling a lyophilized powder of the antibiotic into a vial, preferably together with a stabilizer, and in use, the contents of the vial are dissolved in a dissolving liquid for administration.

The diluent or carrier includes, for example, liquid diluents such as distilled water for injection and physiological isotonic solution, and solid carriers such as lactose, starch, white sugar, glucose, crystalline cellulose, calcium carbonate, kaolin, D-mannitol, magnesium metasilicate aluminate, calcium sulfate, calcium phosphate and bentonite. Addition of stabilizers such as acidic sodium bisulfite is also preferred.

The dosage of the antibiotic substance of this invention can be suitably selected, and is, for example, about 0.01 to about 100 mg/kg/day.

Thus, according to this invention, there can be provided antibiotic compositions for animals other than human, such as poultry, domesticated animals and cultivated fish, and antibiotic compositions for human. These compositions are useful as anitbacterial agents having a broad antibacterial spectrum.

Table 1 below summarizes the antibacterial spectra of several examples of the compound of formula (I) and starting material therefor. i.e., KA-6606 I [compound of formula (II)].

Test compounds

A. 5-O-(3-amino-2-hydroxypropyl)-5-de-O-methyl-Ka-6606 I (Example 1)

B. 5-O-(4-amino-2-hydroxybutyl)-5-de-O-methyl-KA-6606 I. (Example 2)

C. 5-de-O-methyl-5-O-(2,3-dihydroxypropyl)-KA-6606 I. (Example 3)

D. 5-de-O-methyl-5-O-(β-D-glucopyranosyl)-KA-6606 I. (Example 11)

E. 5-O-(3-amino-3-deoxy-α-D-glucopyranosyl)-KA-6606 I. (Example 13)

TABLE 1

| | Minimal inhibitory concentrations (mcg/ml) | | | | | |
|---|---|---|---|---|---|---|
| Test organisms | A | B | C | D | E | KA-6606 I |
| *Staphylococcus aureus* 209P JC-1 | 0.39 | 0.39 | 0.39 | 0.78 | 0.39 | 0.39 |
| *Bacillus anthracis* | ≦0.1 | ≦0.1 | ≦0.1 | 0.2 | 0.2 | 0.2 |
| *cereus* | 0.78 | 1.56 | 3.13 | 6.25 | 0.78 | 1.56 |
| *subtilis* ATCC 6633 | 0.2 | ≦0.1 | 0.2 | 0.39 | 0.2 | 0.2 |
| *Streptococcus faecalis* | 50 | 50 | 100 | >100 | 50 | 25 |
| *Escherichia coli* NIHJ JC-2 | 3.13 | 3.13 | 3.13 | 6.25 | 3.13 | 3.13 |
| K-12 ML1410 | 3.13 | 3.13 | 6.25 | 12.5 | 6.25 | 3.13 |
| R-81[a] | 3.13 | 3.13 | 6.25 | 12.5 | 6.25 | 3.13 |
| R-82[b] | 3.13 | 3.13 | 6.25 | 12.5 | 6.25 | 3.13 |
| R-101[c] | 3.13 | 3.13 | 6.25 | 6.25 | 3.13 | 3.13 |
| R-176[d] | 6.25 | 6.25 | 6.25 | 3.13 | 6.25 | 3.13 |
| JR88/W677[e] | 6.25 | 3.13 | 6.25 | 3.13 | 1.56 | >100 |
| *Proteus vulgaris* OX-19 | 3.13 | 3.13 | 3.13 | 6.25 | 3.13 | 1.56 |
| *Klebsiella pneumoniae* PCI 602 | 1.56 | 1.56 | 0.78 | 3.13 | 1.56 | 1.56 |
| *Pseudomonas aeruginosa* No. 12 | 0.39 | 0.39 | 1.56 | 0.78 | 0.39 | 0.39 |
| No. 99[e] | 6.25 | 6.25 | 25 | 25 | 12.5 | >100 |
| TI-13[a] | 3.13 | 3.13 | 12.5 | 12.5 | 3.13 | 6.25 |
| $A_3$ | 1.56 | 3.13 | 6.25 | 12.5 | 6.25 | 6.25 |
| K-11 | 3.13 | 6.25 | 12.5 | 25 | 3.13 | 12.5 |
| TK-157[b] | 1.56 | 3.13 | 12.5 | 6.25 | 1.56 | 6.25 |
| GN315[f] | 3.13 | 6.25 | 12.5 | 25 | 6.25 | 12.5 |
| *Proteus inconstans* GN1554[g] | 6.25 | 6.25 | 6.25 | 25 | 6.25 | 6.25 |
| *Serratia marcescens* | 1.56 | 1.56 | 3.13 | 3.13 | 1.56 | 3.13 |

(Note)
Resistance mechanism: [a]APH(3')-I,
[b]APH(3')-II
[c]AAD(2")
[d]AAC(3)-II
[e]AAC(3)-I
[f]AAC(6')-IV
[g]AAC(2')

The following Examples illustrate the production of compounds of formula (I) in accordance with this invention.

EXAMPLE 1

Production of 5-O-(3-amino-2-hydroxypropyl)-5-de-O-methyl-KA-6606 I:

(A) One gram of 5-de-O-methyl-KA-6606 II of the following formula

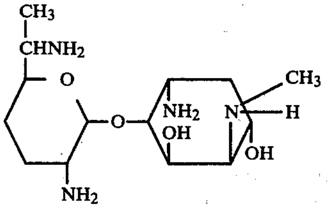

was dissolved in 10 ml of water, and 1.3 g of anhydrous sodium carbonate and 40 ml of methanol were added. Under ice cooling, 2.6 ml of carbobenzoxychloride was added dropwise. The mixture was further stirred for 3 hours under ice cooling, and then the reaction mixture was concentrated to dryness. Chloroform was added to the residue, and the mixture was washed with water and dried. The solvent was then evaporated to give 2.6 g of colorless crystals. Recrystallization from benzene gave 1,4,2',6'-tetrakis-N-benzyloxycarbonyl-5-de-O-methyl-KA-6606 II as colorless needles having a melting point of 153° to 154° C.

Elemental analysis for $C_{46}H_{54}N_4O_{12}$:

| | C | H | N |
|---|---|---|---|
| Calculated (%) | 64.62 | 6.37 | 6.55 |
| Found (%) | 64.49 | 6.33 | 6.61 |

Specific rotation: $[\alpha]_D^{23}+44°$ (c 1, $CHCl_3$)

(B) One hundred milligrams of the N-protected compound obtained in (A) was dissolved in 2 ml of dioxane, and 1.5 ml of a 0.1 M aqueous solution of barium hydroxide was added. The mixture was stirred at 60° C. for 1 hour. The reaction mixture was neutralized with dry ice, and the insoluble materials were removed by filtration. The filtrate was concentrated to dryness. The residue was separated by preparative thin-layer chromatography [plate: Silicagel $PF_{254}$ (Merck & Co.); developing solvent: chloroform/methanol (10/1)] to give 68 mg of 1,2',6'-.

Elemental analysis for: $C_{39}H_{46}N_4O_{11}$:

| | C | H | N |
|---|---|---|---|
| Calculated (%) | 62.72 | 6.21 | 7.50 |
| Found (%) | 62.48 | 6.10 | 7.28 |

Specific rotation: $[\alpha]_D^{23}+33°$ (c 1, $CHCl_3$)

IR($\nu_{max}^{CHCl_3}$, $cm^{-1}$): 1760 (cyclic carbamate).

'H-NMR ($\delta CDCl_3$, ppm): 1.07 (3H, d, J=6 Hz, C—C$\underline{H}_3$), 2.87 (3H, s, N—C$\underline{H}_3$).

(C) One gram of the N,O-protected compound obtained in (B) was dissolved in 20 ml of anhydrous N,N-dimethylformamide, and 2 g of barium oxide and 400 mg of barium hydroxide monohydrate were added. While the mixture was stirred at room temperature, 4 ml of allyl bromide was added dropwise. The mixture was stirred overnight, and neutralized with dry ice. Then, 100 ml of chloroform was added. A white precipitate which formed was removed by centrifugal separation. The supernatant liquid was concentrated to dryness under reduced pressure. The residue was dissolved in 100 ml of chloroform, and washed successively with three 100 ml portions of water. The chloroform layer was dried over sodium sulfate and concentrated under reduced pressure to give 1.2 g of a syrupy crude product. The crude product was purified by preparative thin-layer chromatography [plate: Silicagel $PF_{254}$ (Merck & Co.); developing solvent: chloroform/methanol (19/1)] to give 899 mg of 5-O-allyl-1,2′,6′-tris-N-benzyloxycarbonyl-3-O:4-N-carbonyl-5-de-O-methyl-Ka-6606 II as a syrup.

Elemental analysis for $C_{42}H_{50}N_4O_{11}$:

| | C | H | N |
|---|---|---|---|
| Calculated (%) | 64.11 | 6.40 | 7.12 |
| Found (%) | 64.34 | 6.52 | 6.99 |

Specific rotation: $[\alpha]_D^{20}+40°$ (c 1, $CHCl_3$)

IR ($\nu_{max}^{CHCl_3}$, $cm^{-1}$): 1760 (carbamate), 1710 (—NH—$COOCH_2$— 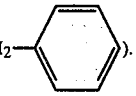).

'H-NMR ($\delta_{CDCl_3}^{TMS}$, ppm): 1.08 (3H, d, J=7.0 Hz, C—$C\underline{H}_3$), 2.84 (3H, s, N—$C\underline{H}_3$), 7.35 (15H, m, phenyl).

(D) 899 mg of the 5-O-allyl-N,O-protected compound obtained in (C) was dissolved in 18 ml of dioxane, and 13.8 ml of 0.34 N barium hydroxide was added. The mixture was stirred overnight at 60° C. Furthermore, 738 mg of barium hydroxide octahydrate was added, and the mixture was reacted for 5 hours. The reaction mixture was neutralized with dry ice, and 80 ml of methanol was added. The resulting white precipitate was removed by centrifugation. The supernatant was concentrated to dryness under reduced pressure. The residue was dissolved in chloroform, and washed with two 100 ml portions of water. The chloroform layer was dried over sodium sulfate, and concentrated to dryness under reduced pressure to give 790 mg of 5-O-allyl-1,2′,6′-tris-N-benzyloxycarbonyl-5-de-O-methyl-KA-6606 II as a syrup. Without purification, this compound was used in the subsequent reaction.

(E) 790 mg of the crude 5-O-allyl compound obtained in (D) was dissolved in 23 ml of dioxane, and 637 mg of N-hydroxysuccinimide ester of N-benzyloxycarbonylglycine and 1.6 ml of triethylamine were added. The mixture was heated at 90° C. for 2 hours. The reaction mixture was concentrated to dryness under reduced pressure. The residue was dissolved in 50 ml of chloroform, and washed with three 50 ml portions of water. The chloroform layer was dried over sodium sulfate, and concentrated to dryness under reduced pressure to give 1.05 g of a solid. The solid was purified by preparative thin-layer chromatography [plate: Silicagel $PF_{254}$ (Merck & Co.); developing solvent: chloroform/methanol (15/1)] to give 612 mg of 5-O-allyl-1,2′,6′-tris-N-benzyloxycarbonyl-4-N-(N-benzyloxycarbonylglycyl)-5-de-O-methyl-KA-6606 II as a syrup.

Elemental analysis for $C_{51}H_{61}N_5O_{13}$:

| | C | H | N |
|---|---|---|---|
| Calculated (%): | 64.34 | 6.46 | 7.36 |
| Found (%): | 64.11 | 6.56 | 7.14 |

Specific rotation: $[\alpha]_D^{24}+35°$ (c 1, $CHCl_3$)

IR ($\nu_{max}^{CHCl_3}$, $cm^{-1}$):

1705 (—$NHCOOCH_2$— 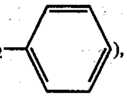), 1635 (amide I).

'H-NMR ($\delta_{CDCl_3}^{TMS}$, ppm): 1.06 (3H, d, J=6.5 Hz, C—$C\underline{H}_3$), 2.90 (3H, s, N—$C\underline{H}_3$), 7.3 (20H, m, phenyl).

(F) 287 mg of the 4-N-protected glycyl compound obtained in (E) was dissolved in 3.0 ml of chloroform. The solution was stirred at room temperature while shutting off light. 210 mg of m-chloroperbenzoic acid was added, and the reaction was carried out for 4 hours. Furthermore, 105 mg of m-chloroperbenzoic acid was added, and the mixture was stirred for 4 hours. Chloroform (20 ml) was added to the reaction mixture, and the mixture was washed with two 5 ml portions of 5 N sodium hydroxide and two 10 ml portions of water. The chloroform layer was dried over sodium sulfate, and concentrated under reduced pressure to give 293 mg of 1,2′,6′-tris-N-benzyloxycarbonyl-4-N-(N-benzyloxycarbonylglycyl)-5-de-O-methyl-5-O-(2,3-epoxypropyl)-KA-6606 II as a colorless syrup.

Elemental analysis for $C_{51}H_{61}N_5O_{14}$:

| | C | H | N |
|---|---|---|---|
| Calculated (%): | 63.28 | 6.35 | 7.23 |
| Found (%): | 63.55 | 6.48 | 7.18 |

Specific rotation: $[\alpha]_D^{25}+38°$ (c 1, $CHCl_3$)

IR ($\nu_{max}^{CHCl_3}$, $cm^{-1}$):

1705 (—$NHCOOCH_2$— 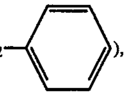), 1640 (amide I).

'H-NMR ($\delta_{CDCl_3}^{TMS}$, ppm): 1.08 (3H, d, J=6.0 Hz, C—$C\underline{H}_3$), 2.96 (3H, s, N—$C\underline{H}_3$), 7.35 (20H, m, phenyl).

(G) 293 mg of the epoxy compound obtained in (F) was dissolved in 16.5 ml of anhydrous N,N-dimethylformamide. Sodium azide (197 mg) was added, and the mixture was stirred overnight at 70° C. The reaction mixture was concentrated to dryness under reduced pressure. The residue was dissolved in 100 ml of chloroform, and washed with four 100 ml portions of water. The chloroform layer was dried over sodium sulfate, and concentrated under reduced pressure to give 312 mg of a syrupy crude product. The crude product was purified by preparative thin-layer chromatography

[plate: Silicagel $PF_{254}$ (Merck & Co.); developing solvent: chloroform/methanol (7/1)] to give 243 mg of 5-O-(3-azido-2-hydroxypropyl)-1,2',6'-tris-N-benzyloxycarbonyl-4-N-(N-benzyloxycarbonylglycyl)-5-de-O-methyl-KA-6606 II as a syrup.

Elemental analysis for $C_{51}H_{62}N_8O_{14}$:

| | C | H | N |
|---|---|---|---|
| Calculated (%) | 60.58 | 6.18 | 11.08 |
| Found (%) | 60.14 | 6.32 | 10.91 |

Specific rotation: $[\alpha]_D^{23}+30°$ (c 1, $CHCl_3$)

IR ($\nu_{max}^{CHCl_3}$, $cm^{-1}$):
2100 (azide), 1705 (—$NHCOOCH_2$— 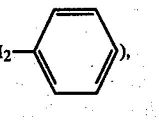 ), 1635 (amide I).

'H-NMR ($\delta_{CDCl_3}^{TMS}$, ppm): 1.08 (3H, d, J=7.0 Hz, C—$C\underline{H}_3$), 2.94 (3H, s, N—$C\underline{H}_3$),
7.36 (20H, m, phenyl).

(H) 243 mg of the azido compound obtained in (G) was dissolved in 3.8 ml of acetic acid, and 243 mg of palladium black was added. Thus, the azido compound was hydrogenolyzed in a stream of hydrogen for 4 hours. After the reaction, the palladium black was removed by filtration. The filtrate was diluted to a volume of 400 ml with ice-cooled water, neutralized with concentrated aqueous ammonia, and adsorbed onto a column (1×25 cm) of CM-Sephadex C-25 ($NH_4^+$ form). The column was washed with deionized water, and then eluted with 120 ml of 0.1 N aqueous ammonia and 120 ml of 0.5 N aqueous ammonia by a concentration gradient method to obtain 4 ml fractions. Fractions Nos. 38 to 52 were combined, and lyophilized to give 49.4 mg of a white solid. The white solid was further adsorbed onto a column of CM-Sephadex C-25 ($NH_4^+$ type). The column was washed with deionized water, and eluted with 1 N aqueous ammonia. Active fractions were collected and lyophilized to give 41.1 mg of 5-O-(3-amino-2-hydroxypropyl)-5-de-O-methyl-KA-6606 I of the following structure as a colorless powder.

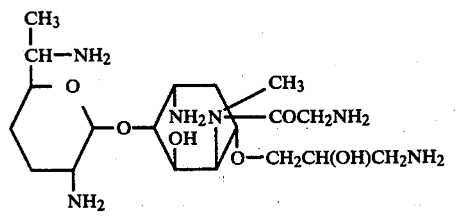

Elemental analysis for $C_{19}H_{40}N_6O_6.1/2H_2CO_3$:

| | C | H | N |
|---|---|---|---|
| Calculated (%): | 48.84 | 8.62 | 17.52 |
| Found (%): | 48.74 | 8.48 | 17.78 |

Specific rotation: $[\alpha]_D^{25}+106°$ (c 1, $H_2O$)
IR ($\nu_{max}^{KBr}$, $cm^{-1}$): 1630 (amide I), 1580 (amide II).
'H-NMR ($\delta_{D_2O}$, ppm, (TMS external standard)): 1.54 (3H, d, J=6.5 Hz, C—$C\underline{H}_3$), 3.55 (3H, s, N—$C\underline{H}_3$), 5.45 (1H, d, J=3.5 Hz, H-1').

EXAMPLE 2

Production of 5-O-(4-amino-2-hydroxybutyl)-5-de-O-methyl-KA-6606 I:

(A) 120 mg of 1,2',6'-tris-N-benzyloxycarbonyl-4-N-(N-benzyloxycarbonylglycyl)-5-de-O-methyl-5-O-(2,3-epoxypropyl)-KA-6606 II obtained in Example 1, (F) was dissolved in 3.6 ml of anhydrous N,N-dimethylformamide, and 80 ml of potassium cyanide was added. The mixture was stirred at 70° C. for 6 hours. The reaction mixture was concentrated to dryness under reduced pressure. The residue was dissolved in 30 ml of chloroform, and washed with three 30 ml portions of water. The chloroform layer was dried over sodium sulfate, and concentrated to dryness under reduced pressure. The residue was purified by preparative thin-layer chromatography [plate: Silicagel $PF_{254}$ (Merck & Co.); developing solvent: chloroform/methanol (10/1)] to give 98 mg of 1,2',6'-tris-N-benzyloxycarbonyl-4-N-(N-benzyloxycarbonylglycyl)-5-O-(3-cyano-2-hydroxypropyl)-5-de-O-methyl-KA-6606 II.

Elemental analysis for $C_{52}H_{62}N_6O_{14}$:

| | C | H | N |
|---|---|---|---|
| Calculated (%): | 62.76 | 6.28 | 8.45 |
| Found (%): | 62.67 | 6.57 | 8.50 |

Specific rotation: $[\alpha]_D^{25}+39°$ (c 1, $CHCl_3$)

IR ($\nu_{max}^{KBr}$ $cm^{-1}$):
2250 (—CN), 1700 (—$NHCOOCH_2$— 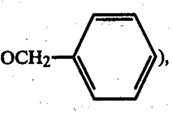 ), 1635 (amide I).

'H-NMR ($\delta_{CDCl_3}^{TMS}$, ppm): 1.08 (3H, d, J=6.5 Hz, C—$C\underline{H}_3$), 2.92 (3H, s, N—$C\underline{H}_3$), 7.35 (20H, m, phenyl), 2.48 (2H, d, J=7.0 Hz, —$C\underline{H}_2$CN).

(B) 98 mg of the cyano compound obtained in (a) was dissolved in 2 ml of acetic acid, and hydrogenolyzed in a stream of hydrogen in the presence of 98 mg of palladium black for 4 hours. After the reaction, the palladium black was removed by filtration, and the residue was catalytically reduced in the presence of Raney nickel for 8 hours at a hydrogen pressure of 4 atmospheres. After the reaction, the reaction mixture was diluted with 100 ml of cold water, and the Raney nickel was removed by filtration. The filtrate was neutralized with concentrated aqueous ammonia, diluted with 500 ml of cold water, and adsorbed onto a column (1×25 cm) of CM-Sephadex C-25 ($NH_4^+$ form). The column was washed with water, then eluted with 120 ml of 0.1 N aqueous ammonia and 120 ml of 0.5 N aqueous ammonia by a concentration gradient method, and further eluted with 60 ml of 0.5 N aqueous ammonia and 120 ml of 0.75 N aqueous ammonia in 5 ml fractions. Fractions Nos. 70 to 91 of the eluate from 0.75 N aqueous ammonia were lyophilized to give 21.0 mg of a white solid. The solid was further adsorbed onto a column of CM-Sephadex C-25 ($NH_4^+$ form). The column was washed with deionized water, and eluted with 1 N aqueous ammonia. Active fractions were lyophilized to give 17.5 mg of 5-O-(4-amino-2-hydroxybutyl)-5-de-O-methyl-KA-6606 I having the following structure as a colorless powder.

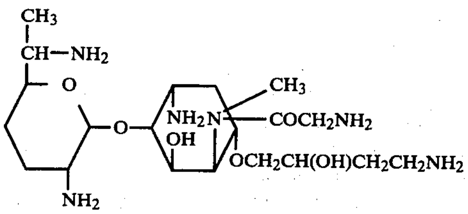

Elemental analysis for $C_{20}H_{42}N_6O_6.1/2H_2CO_3$:

| | C | H | N |
|---|---|---|---|
| Calculated (%): | 49.88 | 8.78 | 17.03 |
| Found (%) | 49.74 | 8.77 | 17.32 |

Specific rotation: $[\alpha]_D^{25}+132°$ (c 0.37, $H_2O$)

IR ($\nu_{max}^{KBr}$, $cm^{-1}$): 1625 (amide I) 1580 (amide II)

'H-NMR ($\delta_{D_2O}$ (TMS external standard), ppm): 1.52 (3H, d, J=7.0 Hz, C—$C\underline{H}_3$), 3.56 (3H, s, N—$C\underline{H}_3$), 5.46 (1H, d, J=3.5 Hz, H-1').

EXAMPLE 3

Production of 5-de-O-methyl-5-O-(2,3-dihydroxy-propyl)-KA-6606 I:

(A) 194 mg of 1,2',6'-tris-N-benzyloxycarbonyl-4-N-(N-benzyloxycarbonylglycyl)-5-de-O-methyl-5-O-(2,3-epoxypropyl)-KA-6606 II obtaned in Example 1, (F) was dissolved in 3.9 ml of acetone, and 1.9 ml of water was added. With stirring, 100 mg of concentrated sulfuric acid was added dropwise at room temperature with stirring. The mixture was further stirred for 4 hours. The reaction mixture was neutralized with 4 N sodium hydroxide. Acetone was evaporated at room temperature under reduced pressure, and 20 ml of chloroform was added. The mixture was washed with 5 ml of 4 N sodium hydroxide and two 20 ml portions of water. The chloroform layer was dried over sodium sulfate, and concentrated under reduced pressure to give 189 mg of a syrupy crude product. The crude product was purified by preparative thin-layer chromatography [plate: Silicagel $PF_{254}$ (Merck & Co.); developing solvent: chloroform/methanol (10/1)] to give 122 mg of 1,2',6'-tris-N-benzyloxycarbonyl-4-N-(N-benzyloxycarbonylglycyl)-5-de-O-methyl-5-O-(2,3-dihydroxy-propyl)-KA-6606 II as a white solid.

Elemental analysis for $C_{51}H_{63}N_5O_{15}$:

| | C | H | N |
|---|---|---|---|
| Calculated (%) | 62.12 | 6.44 | 7.10 |
| Found (%): | 62.00 | 6.58 | 7.04 |

Specific rotation: $[\alpha]_D^{23}+36°$ (c 1, $CHCl_3$)

IR ($\nu_{max}^{CHCl_3}$, $cm^{-1}$):

1705 (—NHCOOCH2— 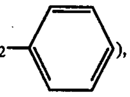 ),

-continued 1635 (amide I).

'H-NMR ($\delta_{CDCl_3}^{TMS}$, ppm): 1.06 (3H, d, J=6.0 Hz, C—$C\underline{H}_3$), 2.91 (3H, s, N—$C\underline{H}_3$), 7.35 (15H, m, phenyl).

(B) 81.4 mg of the N-protected compound obtained in (A) was dissolved in 2.0 ml of acetic acid, and 81.4 mg of palladium black was added. The N-protected compound was hydrogenolyzed in a stream of hydrogen for 4 hours. After the reaction, the palladium black was removed by filtration. The filtrate was diluted to a volumn of 200 ml with ice-cooled water, neutralized with concentrated aqueous ammonia, and adsorbed onto a column (1.0×20 cm) of CM-Sephadex C-25 ($NH_4^+$ form). The column was washed with deionized water, and eluted with 90 ml of 0.15 N aqueous ammonia and 90 ml of 0.5 N aqueous ammonia by a concentration gradient method in 5 ml fractions. Fractions Nos. 19 to 25 were combined, and lyophilized to give 28.1 mg of a white solid. The solid was further adsorbed onto a column of CM-Sephadex C-25 ($NH_4^+$ form). The column was washed with deionized water and eluted with 1 N aqueous ammonia. Active fractions were collected, and lyophilized to give 21.1 mg of 5-de-O-methyl-5-O-(2,3-dihydroxypropyl)-KA-6606 I of the following structure as a colorless powder.

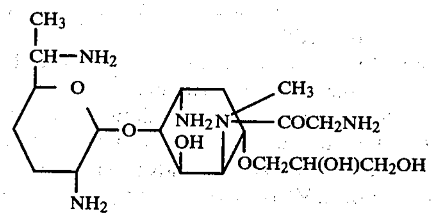

Elemental analysis for $C_{19}H_{39}N_5O_7.H_2O$:

| | C | H | N |
|---|---|---|---|
| Calculated (%) | 48.81 | 8.84 | 14.98 |
| Found (%) | 48.37 | 9.01 | 14.80 |

Specific rotation: $[\alpha]_D^{22}+109°$ (c 0.88, $H_2O$)

IR ($\nu_{max}^{KBr}$, $cm^{-1}$): 1630 (amide I), 1580 (amide II).

'H-NMR ($\delta_{D_2O}$, ppm, (TMS external standard)): 1.52 (3H, d, J=7.0 Hz, C—$C\underline{H}_3$), 3.52 (3H, s, N—$C\underline{H}_3$), 5.39 (1H, d, J=3.5 Hz, H-1').

EXAMPLE 4

Production of 5-de-O-methyl-5-O-(2-hydroxyethyl)-KA-6606 I:

(A) 194 mg of 5-O-allyl-1,2',6'-tris-benzyloxycarbonyl-4-N-(N-benzyloxycarbonylglycyl)-5-de-O-methyl-KA-6606 II obtained in Example 1, (E) was dissolved in 25 ml of chloroform. While the solution was cooled with dry ice-acetone and stirred, ozone gas was passed through it for 20 minutes. Sodium borohydride (62 mg) was dissolved in a cold 50% aqueous solution of ethanol, and the solution was added dropwise to the reaction mixture. The mixture was heated for 1 hour at 50° C. The reaction mixture was left to stand overnight at room temperature and neutralized with 10% sulfuric acid, and chloroform and methanol were evaporated under reduced pressure. The aqueous layer was again acidified, and extracted with chloroform. The chloroform layer was washed with two 50 ml portions of water, dried over sodium sulfate, and concentrated under reduced pressure to give 187 mg of a syrupy crude product. The crude product was purified by preparative thin-layer chromatography [plate: Silicagel $PF_{254}$ (Merck & Co.); developing solvent: chloroform/methanol (10/1)] to give 143 mg of 1,2',6'-tris-N-benzyloxycarbonyl-4-N-(N-benzyloxycarbonylglycyl)-5-de-O-methyl-5-O-(2-hydroxyethyl)-KA-6606 II as a solid.

Elemental analysis for $C_{50}H_{61}N_5O_{14}$:

| | C | H | N |
|---|---|---|---|
| Calculated (%): | 62.81 | 6.43 | 7.33 |
| Found (%): | 62.56 | 6.38 | 7.05 |

Specific rotation: $[\alpha]_D^{23}+43°$ (c 0.38, $CHCl_3$)

IR ($\nu_{max}^{CHCl_3}$, $cm^{-1}$):

1710 ($-NHCOOCH_2-$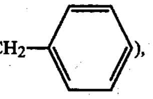), 1640 (amide I).

'H-NMR ($\delta_{CDCl_3}^{TMS}$, ppm): 1.06 (3H, d, J=6.5 Hz, C—$\underline{H_3}$), 2.90 (3H, s, N—C$\underline{H_3}$), 7.3 (20H, m, phenyl).

(B) 70 mg of the N-protected compound obtained in (A) was dissolved in 2.0 ml of acetic acid, and 70 mg of 5% palladium carbon was added. The N-protected compound was hydrogenolyzed in a stream of hydrogen for 6 hours. After the reaction, the catalyst was removed by filtration. The filtrate was diluted to a volumn of 200 ml with cold water, neutralized with concentrated aqueous ammonia, and adsorbed onto a column (1.0×20 cm) of CM-Sephadex C-25 ($NH_4^+$ form). The column was washed with deionized water, and eluted in 5 ml fractions with 90 ml of 0.1 N aqueous ammonia and 90 ml of 0.5 N aqueous ammonia by a concentration gradient method. Fractions Nos. 20 to 25 were collected and lyophilized to give 15.9 mg of a white solid. The solid was further adsorbed onto a column of CM-Sephadex C-25 ($NH_4^+$ form). The column was washed with deionized water, and eluted with 1 N aqueous ammonia. Active fractions were collected and lyophilized to give 12.4 mg of 5-de-O-methyl-5-O-(2-hydroxyethyl)-KA-6606 I of the following structure as a colorless powder.

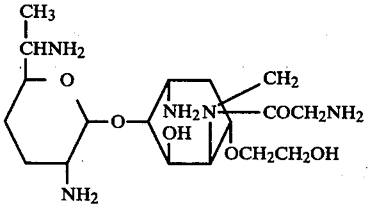

Elemental analysis for $C_{18}H_{37}N_5O_6.H_2O$:

| | C | H | N |
|---|---|---|---|
| Calculated (%): | 49.41 | 8.98 | 16.01 |
| Found (%): | 49.33 | 9.01 | 15.80 |

Specific rotation: $[\alpha]_D^{22}+138°$ (c 0.34, $H_2O$)

IR ($\nu_{max}^{KBr}$, $cm^{-1}$): 1628 (amide I), 1580 (amide II).

'H-NMR ($\delta_{D_2O}$, ppm, (TMS external standard)): 1.52 (3H, d, J=6.5 Hz, C—C$\underline{H_3}$), 3.52 (3H, s, N—C$\underline{H_3}$), 5.40 (1H, d, J=3.5 Hz, H-1').

EXAMPLE 5

Production of 5-O-(2-aminoethyl)-5-de-O-methyl-KA-6606 I:

(A) 140 mg of 1,2',6'-tris-N-benzyloxycarbonyl-4-N-(N-benzyloxycarbonylglycyl)-5-de-O-methyl-5-O-(2-hydroxyethyl)-KA-6606 II obtained in Example 4, (A) was dissolved in 4.2 ml of anhydrous pyridine. With ice cooling and stirring, 115 mg of p-toluenesulfonyl chloride was added, and the mixture was further stirred for 5 hours. Water (0.7 ml) was added to the reaction mixture, and the mixture was left to stand for 1 hour and then concentrated to dryness at room temperature under reduced pressure. The residue was dissolved in 30 ml of chloroform, washed with 30 ml of 0.4 N potassium hydrogen sulfate, 30 ml of 1 N sodium hydrogen carbonate, and then two 30 ml portions of water, dried over sodium sulfate, and concentrated under reduced pressure to give 162 mg of a syrupy crude product. The crude product was purified by preparative thin-layer chromatography [plate: Silicagel $PF_{254}$; developing solvent: chloroform/methanol (95/5)] to give 152 mg of 1,2',6'-tris-N-benzyloxycarbonyl-4-N-(N-benzyloxycarbonylglycyl)-5-de-O-methyl-5-O-(2-tosyloxyethyl)-KA-6606 II as a colorless solid.

Elemental analysis for $C_{57}H_{67}N_5O_{16}S$:

| | C | H | N | S |
|---|---|---|---|---|
| Calculated (%): | 61.66 | 6.08 | 6.31 | 2.89 |
| Found (%): | 61.79 | 6.07 | 6.33 | 2.74 |

Specific rotation: $[\alpha]_D^{24}+32°$ (c 0.5, $CHCl_3$)

IR ($\nu_{max}^{CHCl_3}$, $cm^{-1}$):

1710 ($-NHCOOCH_2-$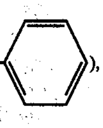), 1640 (amide I), 1175 ($-SO_2-$).

'H-NMR ($\delta_{CDCl_3}^{TMS}$, ppm): 1.08 (3H, d, J=7.0 Hz, C—C$\underline{H_3}$), 2.44

(3H, s, 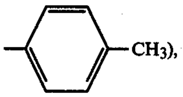$-CH_3$), 2.91 (3H, s, N—C$\underline{H_3}$), 7.4–7.9 (24H, m, phenyl).

(B) 150 mg of the tosyl compound obtained in (A) was dissolved in 4.5 ml of anhydrous N,N-dimethylformamide, and 88 mg of sodium azide was added. The mixture was stirred at 60° C. for 4 hours. The reaction mixture was concentrated to dryness under reduced pressure. The residue was dissolved in 30 ml of chloroform, and washed with three 30 ml portions of water. The chloroform layer was dried over sodium sulfate, and concentrated to dryness under reduced pressure to give 146 mg of a syrupy crude product. The crude product was purified by preparative thin-layer chromatography [plate: Silicagel $PF_{254}$ (Merck & Co.); developing solvent: chloroform/methanol (95/5)] to give 124 mg of 5-O-(2-azidoethyl)-1,2',6'-tris-N-benzyloxycarbonyl)-4-N-(N-benzyloxycarbonylglycyl)-5-de-O-methyl-KA-6606 II as a colorless solid.

Elemental analysis for $C_{50}H_{60}N_8O_{13}$:

| | C | H | N |
|---|---|---|---|
| Calculated (%): | 61.21 | 6.16 | 11.42 |
| Found (%): | 60.92 | 6.02 | 11.44 |

Specific rotation: $[\alpha]_D^{22}+39°$ (c 1, $CHCl_3$)

IR ($\nu_{max}^{CHCl_3}$, $cm^{-1}$):
2090 (azido), 1705 (—$NHCOOCH_2$— 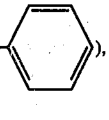), 1635 (amide I).

'H-NMR ($\delta_{CDCl_3}^{TMS}$, ppm): 1.07 (3H, d, J=7.0 Hz, C—$CH_3$), 2.94 (3H, s, N—$CH_3$), 7.3 (20H, m, phenyl).

(C) 124 mg of the azido compound obtained in (B) was dissolved in 20 ml of acetic acid, and 124 mg of palladium black was added. The azido compound was thus hydrogenolyzed in a stream of hydrogen for 7 hours. After the reaction, the catalyst was removed by filtration, and the filtrate was diluted to a volume of 200 ml with ice-cooled water, neutralized with concentrated aqueous ammonia, and adsorbed onto a column (1.0×20 cm) of CM-Sephadex C-25 ($NH_4^+$ form). The column was washed with decarboxylated deionized water, and eluted with 120 ml of 0.1 N aqueous ammonia and 120 ml of 0.5 N aqueous ammonia by a concentration gradient method in 5 ml fractions. Fractions Nos. 29 to 39 were collected and lyophilized to give 31.6 mg of a white solid. The solid was further adsorbed onto a column of CM-Sephadex C-25 ($NH_4^+$ form). The column was washed with deionized water, and eluted with 1 N aqueous ammonia. Active fractions were collected and lyophilized to give 24.6 mg of 5-O-(2-aminoethyl)-5-de-O-methyl-KA-6606 I of the following structure as a colorless powder.

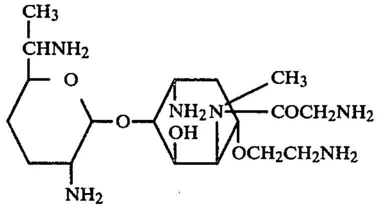

Elemental analysis for $C_{18}H_{38}N_6O_5.H_2O$:

| | C | H | N |
|---|---|---|---|
| Calculated (%) | 49.52 | 9.24 | 19.25 |
| Found (%) | 49.27 | 9.06 | 19.21 |

Specific rotation: $[\alpha]_D^{25}+115°$ (c 1, $H_2O$)
IR ($\nu_{max}^{KBr}$, $cm^{-1}$): 1630 (amide I), 1570 (amide II).

'H-NMR ($\delta_{D_2O}$, ppm, (TMS external standard)): 1.52 (3H, d, J=6.5 Hz, C—$CH_3$), 3.54 (3H, s, N—$CH_3$), 5.45 (1H, d, J=3.0 Hz, H-1').

EXAMPLE 6

Production of 5-O-(3-amino-2-hydroxypropyl)-4-N-glycyl-5-de-O-methyl-KA-6606 VI:

(A) 250 mg of de-O-methyl-KA-6606 VI represented by the following formula

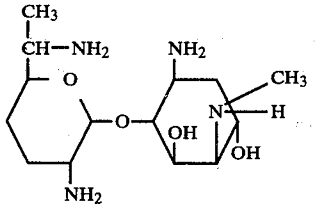

was dissolved in 9 ml of methanol, and 500 mg of nickel acetate tetrahydrate was added. The mixture was stirred for 30 minutes, and then 564 mg of N-(benzyloxycarbonloxy)-succinimide was added. The mixture was stirred at room temperature for 2 hours. To the reaction mixture were added 15 ml of concentrated aqueous ammonia and 15 ml of methanol, and the mixture was stirred for 30 minutes, and concentrated to dryness. Chloroform and 3 N aqueous ammonia were added to the reaction mixture. The chloroform layer was separated, washed with 3 N aqueous ammonia three times and water twice, and dried over sodium sulfate. The solvent was then evaporated. The residue was dissolved in 22 ml of methanol, and a solution of 810 mg of sodium carbonate in 7 ml of water was added. With ice cooling, 0.4 ml of phenoxycarbonyl chloride was added. The mixture was stirred for 2 hours. Furthermore, 800 mg of sodium hydrogen carbonate was added, and the mixture was stirred overnight at room temperature. The reaction mixture was concentrated to dryness. The residue was dissolved in chloroform, washed with water and 4 N sodium hydroxide three times and further with water, and dried over sodium sulfate to evaporate the solvent. The residue was adsorbed onto a column of silica gel, and the column was eluted with chloroform/methanol (50/1). Fractions containing the desired product were concentrated to give 480 mg of 1,2',6'-tris-N-benzyloxycarbonyl-3-O:4-N-carbonyl-5-de-O-methyl-KA-6606 VI as a colorless solid.

Elemental analysis for $C_{39}H_{46}N_4O_{11}$:

| | C | H | N |
|---|---|---|---|
| Calculated (%) | 62.72 | 6.21 | 7.50 |
| Found (%) | 62.54 | 5.96 | 7.43 |

Specific rotation: $[\alpha]_D^{24}+6°$ (c 2, $CHCl_3$)
IR ($\nu_{max}^{CHCl_3}$, $cm^{-1}$): 1765 (cyclic carbamate)
'H-NMR ($\delta_{CDCl_3}^{TMS}$, ppm): 1.12 (3H, d, J=7 Hz, C—$CH_3$), 2.88 (3H, s, N—$CH_3$).

(B) 200 mg of the carbamate compound obtained in (A) was reacted and treated in the same way as in Example 1, (C) to give 182 mg of 5-O-allyl-1,2',6'-tris-N-benzyloxycarbonyl-3-O:4-N-carbonyl-5-de-O-methyl-KA-6606 VI as a colorless solid.

Elemental analysis for $C_{42}H_{50}N_4H_{11}$:

| | C | H | N |
|---|---|---|---|
| Calculated (%) | 64.11 | 6.40 | 7.12 |
| Found (%) | 64.53 | 6.28 | 6.89 |

Specific rotation: $[\alpha]_D^{24}+5°$ (c 2, $CHCl_3$)
IR ($\nu_{max}^{CHCl_3}$, $cm^{-1}$): 1760 (cyclic carbamate).
$^1$H-NMR ($\delta_{CDCl_3}^{TMS}$, ppm):
1.15 (3H, d, J=6.5 Hz, C—$CH_3$), 2.87 (3H, s, N—$CH_3$).

(C) 180 mg of the 5-O-allyl compound obtained in (B) was reacted and treated in the same way as in Example 1, (D) and (E) to give 153 mg of 5-O-allyl-1,2',6'-tris-N-benzyloxycarbonyl-4-N-(N-benzyloxycarbonylglycyl)-5-de-O-methyl-KA-6606 VI as a colorless solid.

Elemental analysis for $C_{51}H_{61}N_5O_{13}$:

| | C | H | N |
|---|---|---|---|
| Calculated (%) | 64.34 | 6.46 | 7.36 |
| Found (%) | 64.33 | 6.28 | 7.06 |

Specific rotation: $[\alpha]_D^{23}+26°$ (c 1, $CHCl_3$)
IR ($\nu_{max}^{CHCl_3}$, $cm^{-1}$):
1635 (amide I).
$^1$H-NMR ($\delta_{CDCl_3}^{TMS}$, ppm): 1.13 (3H, d, J=6.5 Hz, C—$CH_3$), 2.90 (3H, s, N—$CH_3$).

(D) 20 mg of the 5-O-allyl-4-N-glycyl compound obtained in (C) was reacted and treated in the same way as in Example 1, (F) to give 21 mg of 1,2',6'-tris-N-benzyloxycarbonyl-4-N-(N-benzyloxycarbonylglycyl)-5-de-O-methyl-5-O-(2,3-epoxypropyl)-KA-6606 VI as a colorless solid.

Elemental analysis for $C_{51}H_{61}N_5O_{14}$:

| | C | H | N |
|---|---|---|---|
| Calculated (%) | 63.28 | 6.35 | 7.23 |
| Found (%) | 63.18 | 6.33 | 7.15 |

Specific rotation: $[\alpha]_D^{24}+30°$ (c 1, $CHCl_3$)
IR ($\nu_{max}^{CHCl_3}$, $cm^{-1}$). 1635 (amide I).
$^1$H-NMR ($\delta_{CDCl_3}^{TMS}$, ppm): 1.15 (3H, d, J=6 Hz, C—$CH_3$), 2.94 (3H, s, N—$CH_3$).

(E) 150 mg of the epoxy compound obtained in (D) was reacted and treated in the same way as in Example 1, (G) to give 115 mg of 5-O-(3-azido-2-hydroxypropyl)-1,2',6'-tris-N-benzyloxycarbonyl-4-N-(N-benzyloxycarbonylglycyl)-5-de-O-methyl-KA-6606 VI as a colorless solid.

Elemental analysis for $C_{51}H_{62}N_8O_{14}$:

| | C | H | N |
|---|---|---|---|
| Calculated (%) | 60.58 | 6.18 | 11.08 |
| Found (%) | 60.32 | 6.10 | 11.21 |

Specific rotation: $[\alpha]_D^{23}+25°$ (c 1, $CHCl_3$)
IR ($\nu_{max}^{CHCl_3}$, $cm^{-1}$): 2105 (azide), 1635 (amide I).
$^1$H-NMR ($\delta_{CDCl_3}^{TMS}$, ppm): 1.16 (3H, d, J=6.5 Hz, C—$CH_3$), 2.93 (3H, s, N—$CH_3$).

(F) 70 mg of the azido compound obtained in (E) was reacted and treated in the same way as in Example 1, (H) to give 19 mg of 5-O-(3-amino-2-hydroxypropyl)-4-N-glycyl-5-de-O-methyl-KA-6606 VI as a colorless solid represented by the following structural formula.

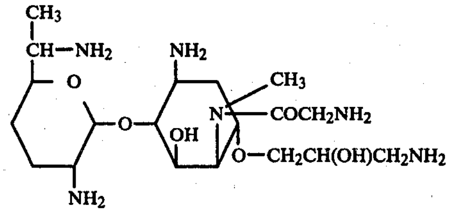

Elemental analysis for $C_{19}H_{40}N_6O_6.H_2CO_3$:

| | C | H | N |
|---|---|---|---|
| Calculated (%) | 47.05 | 8.29 | 16.46 |
| Found (%) | 47.18 | 8.15 | 15.98 |

Specific rotation: $[\alpha]_D^{23}+12.2°$ (c 1, $H_2O$)
IR ($\nu_{max}^{KBr}$, $cm^{-1}$): 1630 (amide I), 1575 (amide II).
$^1$H-NMR ($\delta_{D_2O}$ ppm, (TMS external standard)): 1.53 (3H, d, J=6.5 Hz, C—$CH_3$), 3.60 (3H, s, N—$CH_3$), 5.41 (1H, d, J=3.5 Hz, H-1').

EXAMPLE 7

Production of 5-O-(3-amino-2-hydroxypropyl)-5-de-O-methyl-KA-7038 I:

(A) 70 mg of 5-de-O-methyl-KA-7038 III represented by the following formula

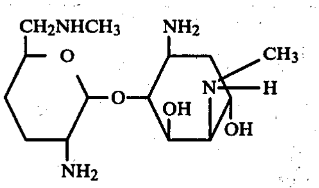

was reacted and treated in the same way as in Example 6, (A) to give 125 mg of 1,2',6'-tris-N-benzyloxycarbonyl-3-O:4-N-carbonyl-5-de-O-methyl-KA-7038 III as a colorless solid.

Elemental analysis for $C_{39}H_{46}N_4O_{11}$:

| | C | H | N |
|---|---|---|---|
| Calculated (%) | 62.72 | 6.21 | 7.50 |
| Found (%) | 62.81 | 6.35 | 7.28 |

Specific rotation: $[\alpha]_D^{24}+8°$ (c 3, $CHCl_3$)
IR ($\nu_{max}^{CHCl_3}$, $cm^{-1}$): 1765 (cyclic carbamate)
$^1$H-NMR ($\delta_{CDCl_3}^{TMS}$, ppm):
2.81 (3H, s, N—$CH_3$), 2.90 (3H, s, N—$CH_3$).

(B) 105 mg of the carbamate compound obtained in (A) was reacted and treated in the same way as in Example 1, (C) to give 93 mg of 5-O-allyl-1,2',6'-tris-N-benzyloxycarbonyl-3-O:4-N-carbonyl-5-de-O-methyl-KA-7038 III as a colorless solid.

Elemental analysis for $C_{42}H_{50}N_4O_{11}$:

| | C | H | N |
|---|---|---|---|
| Calculated (%) | 64.11 | 6.40 | 7.12 |
| Found (%) | 64.09 | 6.12 | 6.88 |

Specific rotation: $[\alpha]_D^{23}+6°$ (c 3, $CHCl_3$)
IR ($\nu_{max}^{CHCl_3}$, $cm^{-1}$): 1765 (cyclic carbamate)

'H-NMR ($\delta_{CDCl_3}^{TMS}$, ppm): 2.82 (3H, s, N—$CH_3$), 2.91 (3H, s, N—$CH_3$).

(C) 30 mg of the 5-O-allyl compound obtained in (B) was reacted and treated in the same way as in Example 1, (D) and (E) to give 22 mg of 5-O-allyl-1,2',6'-tris-N-benzyloxycarbonyl-4-N-(N-benzyloxycarbonylglycyl)-5-de-O-methyl-KA-7038 III as a colorless solid.

Elemental analysis for $C_{51}H_{61}N_5O_{13}$:

| | C | H | N |
|---|---|---|---|
| Calculated (%) | 64.34 | 6.46 | 7.36 |
| Found (%) | 64.15 | 6.52 | 7.27 |

Specific rotation: $[\alpha]_D^{24}+33°$ (c 1, $CHCl_3$)
IR ($\nu_{max}^{CHCl_3}$, $cm^{-1}$): 1635 (amide I).
'H-NMR ($\delta_{CDCl_3}^{TMS}$, ppm): 2.91 (6H, s, N—$CH_3$).

(D) 72 mg of 5-O-allyl-4-N-glycyl compound obtained in (C) was reacted and treated in the same way as in Example 1, (F) to give 70 mg of 1,2',6'-tris-N-ben zyloxycarbonyl-4-N-(N-benzyloxycarbonylglycyl)-5-de-O-methyl-5-O-(2,3-epoxypropyl)-KA-7038 III as a colorless solid.

Elemental analysis for $C_{51}H_{61}N_5O_{14}$:

| | C | H | N |
|---|---|---|---|
| Calculated (%) | 63.28 | 6.35 | 7.23 |
| Found (%) | 62.93 | 6.22 | 7.06 |

Specific rotation: $[\alpha]_D^{23}+41°$ (c 1, $CHCl_3$)
IR ($\nu_{max}^{CHCl_3}$, $cm^{-1}$): 1630 (amide I).
'H-NMR ($\delta_{CDCl_3}^{TMS}$, ppm): 2.89 (3H, s, N—$CH_3$), 2.91 (3H, s, N—$CH_3$).

(E) 50 mg of the epoxy compound obtained in (D) was reacted and treated in the same way as in Example 1, (G) to give 42 mg of 5-O-(3-azido-2-hydroxypropyl)-1,2',6'-tris-N-benzyloxycarbonyl-4-N-(N-benzyloxycarbonylglycyl)-5-de-O-methyl-KA-7038 III as a colorless solid.

Elemental analysis for $C_{51}H_{62}N_8O_{14}$:

| | C | H | N |
|---|---|---|---|
| Calculated (%) | 60.58 | 6.18 | 11.08 |
| Found (%) | 60.04 | 5.87 | 11.13 |

Specific rotation: $[\alpha]_D^{24}+38°$ (c 1, $CHCl_3$)
IR ($\nu_{max}^{CHCl_3}$, $cm^{-1}$): 2100 (azide), 1630 (amide I).
'H-NMR($\delta_{CDCl_3}^{TMS}$, ppm): 2.92 (3H, s, N—$CH_3$).

(F) 55 mg of the azido compound obtained in (E) was reacted and treated in the same way as in Example 1, (H) to give 11 mg of 5-O-(3-amino-2-hydroxypropyl)-5-de-O-methyl-KA-7038 I as a colorless solid having the following structural formula.

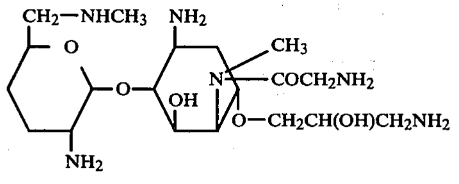

Elemental analysis for $C_{19}H_{40}N_6O_6.H_2CO_3$:

| | C | H | N |
|---|---|---|---|
| Calculated (%) | 47.05 | 8.29 | 16.46 |
| Found (%) | 46.68 | 8.42 | 16.19 |

Specific rotation: $[\alpha]_D^{24}+126°$ (c 0.5, $H_2O$)
IR ($\nu_{max}^{KBr}$, $cm^{-1}$): 1630 (amide I), 1575 (amide II).
'H-NMR ($\delta_{CDCl_3}$, ppm, (TMS external standard)): 2.83 (3H, s, N—$CH_3$), 3.60 (3H, s, N—$CH_3$), 5.41 (1H, d, J=3.3 Hz, H-1').

EXAMPLE 8

Production of 5-de-O-methyl-5-O-($\alpha$-D-glucopyranosyl)-KA-6606 II:

(A) 1.17 g of 1,2',6'-tris-N-benzyloxycarbonyl-3-O:4-N-carbonyl-5-de-O-methyl-KA-6606 II obtained in Example 1, (B) 902 mg of silver perchlorate and 0.57 ml of $\gamma$-collidine were dissolved in 35 ml of anhydrous benzene, and 2.4 g of 2,3,4,6-tetra-O-benzyl-D-glucopyranosyl chloride was added. The mixture was stirred at 80° C. for 3 hours. The insoluble materials were removed from the reaction mixture by filtration. The filtrate was washed with water, and concentrated to dryness. The residue was adsorbed onto a column of silica gel, and the column was eluted with benzene/ethyl acetate (2/1). That portion of the eluate which came out first was worked up in a customary manner to give 1.10 g of 5-O-(2,3,4,6-tetra-O-benzyl-$\alpha$-D-glucopyranosyl)-1,2',6'-tris-N-benzyloxycarbonyl-3-O:4-N-carbonyl-5-de-O-methyl-KA-6606 II as a colorless solid.

Elementary analysis for $C_{73}H_{80}N_4O_{16}$:

| | C | H | N |
|---|---|---|---|
| Calculated (%) | 69.07 | 6.35 | 4.41 |
| Found (%) | 68.73 | 6.66 | 4.25 |

Specific rotation: $[\alpha]_D^{23}+17°$ (c 1, $CHCl_3$)
IR ($\nu_{max}^{CHCl_3}$, $cm^{-1}$): 1760 (cyclic carbamate).
'H-NMR ($\delta_{CDCl_3}^{TMS}$, ppm): 1.19 (3H, d, J=6.5 Hz, C—$CH_3$), 2.61 (3H, s, N—$CH_3$).

That portion of the eluate which came out later was worked up in a customary manner to give 418 mg of 5-O-(2,3,4,6-tetra-O-benzyl-$\beta$-D-glucopyranosyl)-1,2',6'-tris-N-benzyloxycarbonyl-3-O:4-N-carbonyl-5-de-O-methyl-KA-6606 II as a colorless solid.

Elemental analysis for $C_{73}H_{80}N_4O_{16}$:

| | C | H | N |
|---|---|---|---|
| Calculated (%) | 69.07 | 6.35 | 4.41 |
| Found (%) | 69.30 | 6.51 | 4.18 |

Specific rotation: $[\alpha]_D^{23}+6.0°$ (c 1, $CHCl_3$)
IR ($\nu_{max}^{CHCl_3}$, $cm^{-1}$): 1760 (cyclic carbamate).
'H-NMR($\delta_{CDCl_3}^{TMS}$, ppm): 1.12 (3H, d, J=6.5 Hz, C—$CH_3$), 2.73 (3H, s, N—$CH_3$).

(B) 505 mg of the $\alpha$-D-glycopyranosyl compound obtained in (A) was dissolved in 12 ml of anhydrous tetrahydrofuran. The solution was cooled to −40° C., and 24 ml of liquid ammonia was added. Then, 0.5 g of sodium was added. The mixture was stirred at the above temperature for 2.5 hours. Further, 1.5 ml of anhydrous methanol and then 15 ml of water were added, and the mixture was left to stand overnight. After the reaction, the solvent was evaporated. The residue was dissolved in 6 ml of a 1 N aqueous solution of sodium hydroxide, and heated at 100° C. for 4 hours. The reaction mixture was neutralized with hydrochloric acid, diluted with 300 ml of water, and charged onto a column of Amberlite IRC-50 ($NH_4^+$ form). The column was washed with water, and then eluted with 1.5 N aqueous ammonia. The eluates were combined and charged onto a column of CM-Sephadex C-25 ($NH_4^+$ form). The column was eluted by a concentration gradient method using 0.1 N aqueous ammonia and 0.4 N aqueous ammonia. Fractions containing the desired product were collected and lyophilized to give 170 mg of 5-de-O-methyl-5-O-(α-D-glucopyranosyl)-KA-6606 II as a colorless powder having the following structural formula

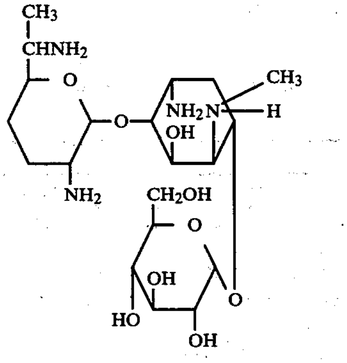

Elemental analysis for $C_{20}H_{40}N_4O_9.H_2O$:

| | C | H | N |
|---|---|---|---|
| Calculated (%) | 48.18 | 8.49 | 11.24 |
| Found (%) | 48.55 | 8.21 | 11.03 |

Specific rotation: $[\alpha]_D^{23}+188°$ (c 1, $H_2O$)
'H-NMR ($\delta_{D_2O}^{TMS}$, ppm): 1.55 (3H, d, J=6.5 Hz, C—$\underline{CH_3}$), 2.89 (3H, s, N—$\underline{CH_3}$), 5.49 (1H, d, J=3.4 Hz, H-1'), 5.69 (1H, d, J=3.6 Hz, Glu-H-1).

EXAMPLE 9

Production of 5-de-O-methyl-5-O-(α-D-glucopyranosyl)-KA-6606 I:

(A) 57 mg of 5-de-O-methyl-5-O-(α-D-glycopyranosyl)-KA-6606 II obtained in Example 8, (B) was dissolved in 1.7 ml of methanol, and 59 mg of nickel acetate was added. The mixture was stirred at room temperature for 30 minutes, and then 82 mg of N-(benzyloxycarbonyloxy)-succinimide was added. The mixture was then stirred for 3 hours. Concentrated aqueous ammonia (0.5 ml) was added, and the mixture was stirred for 30 minutes. The solvent was evaporated, and the residue was dissolved in 10 ml of chloroform, washed with four portions of 3 N aqueous ammonia and two portions of water, and dried to evaporate the solvent. The residue was dissolved in 3 ml of dioxane, and 100 mg of N-hydroxysuccinimide ester of N-benzyloxycarbonylglycine and 0.1 ml of triethylamine were added. The mixture was heated overnight at 37° C. After the reaction, the solvent was evaporated. The residue was dissolved in 10 ml of chloroform, and washed with water, followed by evaporating the solvent. The residue was dissolved in 2 ml of methanol, and 0.7 ml of concentrated aqueous ammonia was added. The mixture was stirred at room temperature for 1 hour. The solvent was evaporated, and the residue was adsorbed onto a column of silica gel. The column was eluted with chloroform/methanol (20/1), and the eluate was worked up in a customary manner to give 50 mg of tetrakis-N-benzyloxycarbonyl-5-de-O-methyl-5-O-(α-D-glucopyranosyl)-KA-6606 I as a colorless solid.

Elemental analysis for $C_{54}H_{67}N_5O_{18}$:

| | C | H | N |
|---|---|---|---|
| Calculated (%) | 60.38 | 6.29 | 6.52 |
| Found (%) | 60.18 | 6.55 | 6.26 |

Specific rotation: $[\alpha]_D^{25}+72°$ (c 1, $CHCl_3$)
IR ($\nu_{max}^{CHCl_3}$, $cm^{-1}$): 1635 (amide I),
'H-NMR ($\delta_{CDCl_3}^{TMS}$, ppm): 1.05 (3H, d, J=6.5 Hz, C—$\underline{CH_3}$), 2.97 (3H, s, N—$\underline{CH_3}$).

(B) 46 mg of the N-protected compound obtained in (A) was dissolved in 1.2 ml of acetic acid, and 20 mg of palladium black was added. Thus, the N-protected compound was hydrogenolyzed in a stream of hydrogen for 4 hours. The reaction mixture was filtered. The filtrate was diluted with 120 ml of water, neutralized with aqueous ammonia, and adsorbed onto a column of CM-Sephadex C-25 ($NH_4^+$ form). The column was eluted by a concentration gradient method using 0.1 N aqueous ammonia and 0.3 N aqueous ammonia. Fractions containing the desired product were collected and lyophilized to give 10 mg of 5-de-O-methyl-5-O-(α-D-glucopyranosyl); KA-6606 I as a colorless powder having the following structural formula.

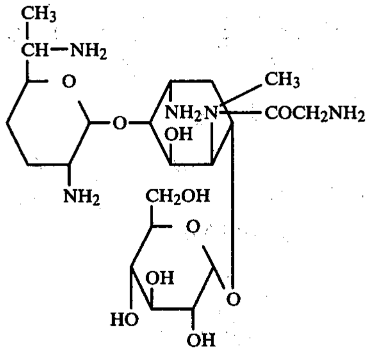

Elemental analysis for $C_{22}H_{43}N_5O_{10}.H_2O$:

| | C | H | N |
|---|---|---|---|
| Calculated (%) | 47.56 | 8.16 | 12.61 |
| Found (%) | 47.18 | 8.33 | 12.36 |

Specific rotation: $[\alpha]_D^{23}+189°$ (c 0.5, $H_2O$)
'H-NMR ($\delta_{D_2O}^{TMS}$, ppm): 1.63 (3H, d, J=6.5 Hz, C—$\underline{CH_3}$), 3.61 (3H, s, N—$\underline{CH_3}$), 5.47 (1H, d, J=3.4 Hz, H-1'), 5.66 (1H, d, J=3.6 Hz, Glu-H-1).

EXAMPLE 10

Production of 5-de-O-methyl-5-O-(β-D-glucopyranosyl)-KA-6606 II:

When 382 mg of 5-O-(2,3,4,6-tetra-O-benzyl-β-D-glucopyranozyl)-1,2',6'-tris-N-benzyloxycarbonyl-3-O:4-N-carbonyl-5-de-O-methyl-KA-6606 II obtained in Example 8, (A) was reacted and treated in the same way as in Example 8, (B) 90 mg of 5-de-O-methyl-5-O-(β-D-glucopyranosyl)-KA-6606 II having the following structural formula was obtained as a colorless powder.

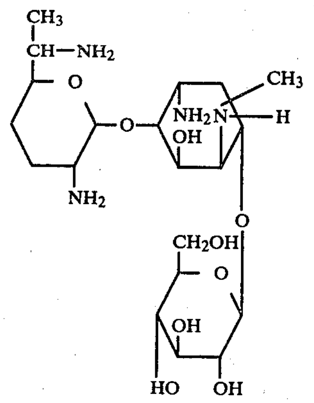

Elemental analysis for $C_{20}H_{40}N_4O_9.H_2O$:

| | C | H | N |
|---|---|---|---|
| Calculated (%) | 48.18 | 8.49 | 11.24 |
| Found (%) | 48.52 | 8.77 | 10.93 |

Specific rotation: $[\alpha]_D^{23}+110°$ (c 0.5, $H_2O$)

'H-NMR ($\delta_{D2O}^{TMS}$, ppm): 1.56 (3H, d, J=6.5 Hz, C—$CH_3$), 2.87 (3H, s, N—$CH_3$), 5.12 (1H, d, J=7.4 Hz, Glu-H-1), 5.46 (1H, d, J=3.4 Hz, H-1').

EXAMPLE 11

Production of 5-de-O-methyl-5-O-(β-D-glucopyranosyl)-KA-6606 I:

(A) When 72 mg of 5-de-O-methyl-5-O-(β-D-glucopyranosyl)-KA-6606 II obtained in Example 10 was reacted and treated in the same way as in Example 9, (A), 63 mg of tetrakis-N-benzyloxycarbonyl-5-de-O-methyl-5-O-(β-D-glucopyranosyl)-KA-6606 I was obtained as a colorless solid.

Elemental analysis for $C_{54}H_{67}N_5O_{18}$:

| | C | H | N |
|---|---|---|---|
| Calculated (%) | 60.38 | 6.29 | 6.52 |
| Found (%) | 60.66 | 6.08 | 6.21 |

Specific rotation: $[\alpha]_D^{25}+25°$ (c 1, $CHCl_3$)

IR ($\nu_{max}^{CHCl_3}$, $cm^{-1}$): 1630 (amide I).

'H-NMR ($\delta_{CDCl_3}^{TMS}$, ppm): 1.02 (3H, d, J=6.5 Hz, C—$CH_3$), 2.95 (3H, s, N—$CH_3$).

(B) 58 mg of the N-protected compound obtained in (A) was reacted and treated in the same way as in Example 9, (B) to give 15 mg of 5-de-O-methyl-5-O-(β-D-glucopyranosyl)-KA-6606 I as a colorless powder having the following structural formula.

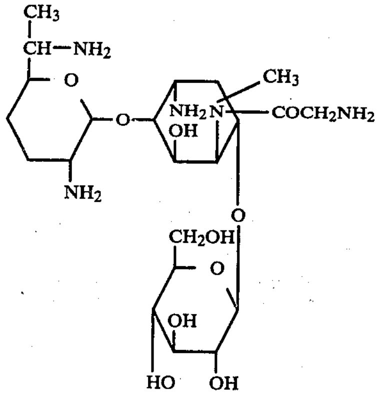

Elemental analysis for $C_{22}H_{43}N_5O_{10}.H_2O$:

| | C | H | N |
|---|---|---|---|
| Calculated (%) | 47.56 | 8.16 | 12.61 |
| Found (%) | 47.23 | 8.38 | 12.29 |

Specific rotation: $[\alpha]_D^{23}+80°$ (c 1, $H_2O$)

'H-NMR ($\delta_{D2O}^{TMS}$, ppm): 1.56 (3H, d, J=6.5 Hz, C—$CH_3$), 3.60 (3H, s, N—$CH_3$), 5.11 (1H, d, J=7.4 Hz, Glu-H-1), 5.45 (1H, d, J=3.4 Hz, H-1').

EXAMPLE 12

Production of 5-O-(3-amino-3-deoxy-α-D-glucopyranosyl)-5-de-O-methyl-KA-6606 II:

(A) 1.28 g of 1,2',6'-tris-N-benzyloxycarbonyl-3-O:4-N-carbonyl-5-de-O-methyl-KA-6606 II obtained in Example 1, (B) and 3.0 g of 2,4,6-tri-O-benzyl-3-benzyloxycarbonylamino-3-deoxy-D-glucopyranosylchloride (Japanese Laid-Open Patent Publication No. 52060/1979, Example 2) were reacted and treated in the same way as in Example 8, (A). From that portion of the eluate which came out first, 1.08 g of 5-O-(2,4,6-tri-O-benzyl-3-benzyloxycarbonylamino-3-deoxy-α-D-glucopyranosyl)-1,2',6'-tris-N-benzyloxycarbonyl-3-O:4-N-carbonyl-5-de-O-methyl-KA-6606 II was obtained as a colorless solid.

Elemental analysis for $C_{74}H_{81}N_5O_{17}$:

| | C | H | N |
|---|---|---|---|
| Calculated (%) | 67.72 | 6.22 | 5.34 |
| Found (%) | 67.45 | 6.08 | 5.11 |

Specific rotation: $[\alpha]_D^{23}+21°$ (c 1, $CHCl_3$)

IR ($\nu_{max}^{CHCl_3}$, $cm^{-1}$): 1760 (cyclic carbamate).

'H-NMR ($\delta_{CDCl_3}^{TMS}$, ppm): 1.13 (3H, d, J=6.5 Hz, C—$CH_3$), 2.56 (3H, s, N—$CH_3$).

From that portion of the eluate which came out later, 405 mg of 5-O-(2,4,6-tri-O-benzyl-3-benzyloxycarbonylamino-3-deoxy-β-D-glucopyranosyl)-1,2',6'-tris-N-benzyloxycarbonyl-3-O:4-N-carbonyl-5-de-O-methyl-KA-6606 II was obtained as a colorless solid.

Elemental analysis for $C_{74}H_{81}N_5O_{17}$:

| | C | H | N |
|---|---|---|---|
| Calculated (%) | 67.72 | 6.22 | 5.34 |
| Found (%) | 67.39 | 6.51 | 5.21 |

Specific rotation: $[\alpha]_D^{23}+13°$ (c 1, $CHCl_3$)
IR ($\nu_{max}^{CHCl_3}$, $cm^{-1}$): 1760 (cyclic carbamate).
'H-NMR ($\delta_{CDCl_3}^{TMS}$, ppm): 1.08 (3H, d, J=6.5 Hz, C—$CH_3$), 2.72 (3H, s, N—$CH_3$).

(B) 500 mg of the α-D-glucopyranosyl compound obtained in (A) was reacted and treated in the same way as in Example 8, (A) to give 160 mg of 5-O-(3-amino-3-deoxy-α-D-glucopyranosyl)-5-de-O-methyl-KA-6606 II as a colorless powder having the following structural formula.

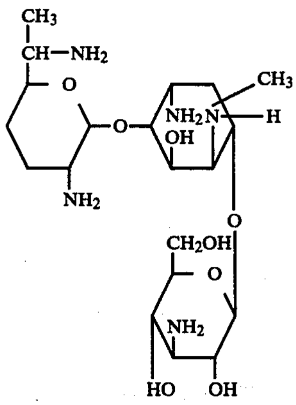

Elemental analysis for $C_{20}H_{41}H_5O_8.H_2O$:

| | C | H | N |
|---|---|---|---|
| Calculated (%) | 48.28 | 8.71 | 14.08 |
| Found (%) | 47.95 | 8.53 | 14.40 |

Specific rotation: $[\alpha]_D^{23}$ +185° (c 1, $H_2O$)
'H-NMR ($\delta_{D_2O}^{TMS}$, ppm):
1.56 (3H, d, J=6.5 Hz, C—$CH_3$), 2.89 (3H, s, N—$CH_3$), 5.47 (1H, d, J=3.4 Hz, H-1'), 5.62 (1H, d, J=3.6 Hz, Glu-H-1).

EXAMPLE 13

Production of 5-O-(3-amino-3-deoxy-α-D-glucopyranosyl)-5-de-O-methyl-KA-6606 I:

(A) 101 mg of 5-O-(3-amino-3-deoxy-α-D-glucopyranosyl)-5-de-O-methyl-KA-6606 II obtained in Example 12, (B) was dissolved in 3 ml of methanol. The solution was cooled to −5° C., and 200 mg of N-(benzyloxycarbonyloxy)succinimide was added. The mixture was stirred for 4 hours. The same reagent (25 mg) was further added, and the mixture was stirred for 2 hours. After the reaction, 0.5 ml of concentrated aqueous ammonia was added, and the mixture was stirred for 30 minutes. The solvent was evaporated, and the residue was dissolved in 10 ml of chloroform, washed with water and dried. The solvent was then evaporated. The residue was dissolved in 1.5 ml of dioxane, and 50 mg of N-hydroxysuccinimide ester of N-benzyloxycarbonyl glycine and 0.05 ml of triethylamine were added. The mixture was heated at 90° C. for 4 hours. After the reaction, the solvent was evaporated. The residue was dissolved in 10 ml of chloroform, and washed with water. After evaporating the solvent, the residue was dissolved in 2 ml of methanol, and 0.4 ml of concentrated aqueous ammonia was added. The mixture was stirred at room temperature for 30 minutes. The solvent was evaporated, and the residue was charged onto a column of silica gel. The column was eluted with chloroform/methanol (20/1), and treated in a customary manner to give 32 mg of testrakis-N-benzyloxycarbonyl-5-O-(3-benzyloxycarbonylamino-3-deoxy-α-D-glucopyranosyl)-5-de-O-methyl-KA-6606 I as a colorless solid.

Elemental analysis for $C_{62}H_{74}N_6O_{19}$:

| | C | H | N |
|---|---|---|---|
| Calculated (%) | 61.68 | 6.18 | 6.96 |
| Found (%) | 61.38 | 6.42 | 6.75 |

Specific rotation: $[\alpha]_D^{23}+71°$ (c 0.8, $CHCl_3$)
IR($\nu_{max}^{CHCl_3}$, $cm^{-1}$): 1630 (amide I).
'H-NMR ($\delta_{CDCl_3}^{TMS}$, ppm): 1.07 (3H, d, J=6.5 Hz, C—$CH_3$). 2.98 (3H, s, N—$CH_3$).

(B) 43 mg of the N-protected compound obtained in (A) was reacted and treated in the same way as in Example 9, (B) to give 11 mg of 5-O-(3-amino-3-deoxy-α-D-glucopyranosyl)-5-de-O-methyl-KA-6606 I as a colorless solid having the following structural.

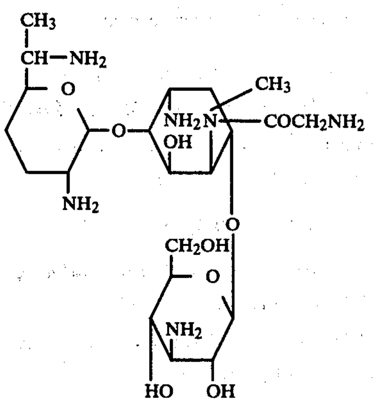

Elemental analysis for $C_{22}H_{44}N_6O_9.H_2O$:

| | C | H | N |
|---|---|---|---|
| Calculated (%) | 47.64 | 8.36 | 15.15 |
| Found (%) | 47.33 | 8.52 | 14.89 |

Specific rotation: $[\alpha]_D^{22}+188°$ (c 0.6, $H_2O$)
'H-NMR ($\delta_{D_2O}^{TMS}$, ppm): 1.54 (3H, d, J=6.5 Hz, C—$CH_3$), 3.60 (3H, s, N—$CH_3$), 5.42 (1H, d, J=3.4 Hz, H-1'), 5.57 (1H, d, J=3.6 Hz, Glu-H-1).

EXAMPLE 14

Production of 5-O-(3-amino-3-deoxy-β-D-glucopyranosyl)-5-de-O-methyl-KA-6606 II:

When 400 mg of 5-O-(2,4,6-tri-O-benzyl-3-benzyloxycarbonyl-amino-3-deoxy-β-D-glucopyranosyl)-1,2',6'-tris-N-benzyloxycarbonyl-3-O:4-N-carbonyl-5-de-O-methyl-KA-6606 II obtained in Example 12, (A) was reacted and treated in the same way as in Example 8, (B), 110 mg of 5-O-(3-amino-3-deoxy-β-D-glucopyranosyl)-5-de-O-methyl-KA-6606 II having the following structural formula was obtained as a colorless powder.

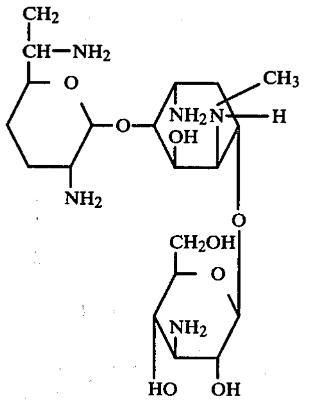

Elemental analysis for $C_{20}H_{41}N_5O_8.H_2O$:

| | C | H | N |
|---|---|---|---|
| Calculated (%) | 48.28 | 8.71 | 14.08 |
| Found (%) | 48.51 | 8.42 | 13.75 |

Specific rotation: $[\alpha]_D^{23}+105°$ (c 1, $H_2O$)

'H-NMR ($\delta_{D2O}^{TMS}$, ppm): 1.58 (3H, d, J=6.5 Hz, C—$\underline{CH_3}$), 2.88 (3H, s, N—$\underline{CH_3}$), 5.12 (1H, d, J=8.0 Hz, Glu-H-1), 5.47 (1H, d, J=3.4 Hz, H-1').

EXAMPLE 15

Production of 5-O-(3-amino-3-deoxy-β-D-glucopyranosyl)-5-de-O-methyl-KA-6606 I:

(A) When 105 mg of 5-O-(3-amino-3-deoxy-β-D-glucopyranosyl)-5-de-O-methyl-KA-6606 II obtained in Example 14 was reacted and treated in the same way as in Example 9, (A), 33 mg of tetrakis-N-benzyloxycarbonyl-5-O-(3-benzyloxycarbonylamino-3-deoxy-β-D-glucopyranosyl-5-de-O-methyl-KA-6606 I was obtained as a colorless solid.

Elemental analysis for $C_{62}H_{74}N_6O_{19}$:

| | C | H | N |
|---|---|---|---|
| Calculated (%) | 61.68 | 6.18 | 6.96 |
| Found (%) | 61.43 | 6.51 | 6.68 |

Specific rotation: $[\alpha]_D^{23}+24°$ (c 1, $CHCl_3$)

IR ($\nu_{max}^{CHCl3}$, $cm^{-1}$): 1630 (amide I).

'H-NMR ($\delta_{CDCl3}^{TMS}$, ppm): 1.06 (3H, d, J=6.5 Hz, C—$\underline{CH_3}$), 2.96 (3H, s, N—$\underline{CH_3}$).

(B) 32 mg of the N-protected compound obtained in (A) was reacted and treated in the same way as in Example 9, (B) to give 8.5 mg of 5-O-(3-amino-3-deoxy-β-D-glucopyranosyl)-5-de-O-methyl-KA-6606 I as a colorless powder having the following structural formula,

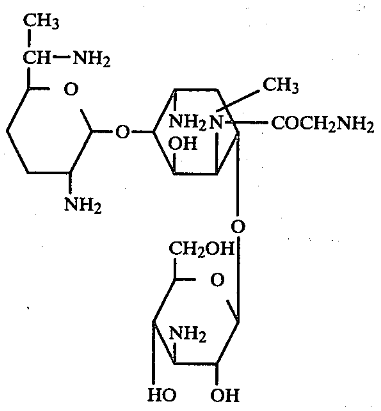

Elemental analysis for $C_{22}H_{44}N_6O_9.H_2O$:

| | C | H | N |
|---|---|---|---|
| Calculated (%) | 47.64 | 8.36 | 15.15 |
| Found (%) | 47.31 | 8.06 | 15.02 |

Specific rotation: $[\alpha]_D^{23}+78°$ (c 0.5, $H_2O$)

'H-NMR ($\delta_{D2O}^{TMS}$, ppm): 1.55 (3H, d, J=6.5 Hz, C—$\underline{CH_3}$), 3.58 (3H, s, N—$\underline{CH_3}$), 5.10 (1H, d, J=8.0 Hz, Glu-$\underline{H}$-1), 5.47 (1H, d, J=3.4 Hz, H-1').

EXAMPLE 16

Production of 5-O-[(S)-3-amino-2-hydroxypropyl]-5-de-O-methyl-KA-6606 I:

(A) Two grams of 1,2',6'-tris-N-benzyloxycarbonyl-3-O:4-N-carbonyl-5-de-O-methyl-KA-6606 II obtained in Example 1, (B) was dissolved in 30 ml of acetic acid, and 1 g of 5% palladium carbon was added. Thus, the above compound was catalytically reduced at room temperature and atmospheric pressure. After the reaction, the catalyst was removed by filtration. The filtrate was concentrated to dryness and dissolved in 200 ml of water. The solution was neutralized with aqueous ammonia, and charged onto a column filled with 90 ml of CM-Sephadex C-25 ($NH_4^+$ form). The column was eluted by a concentration gradient method using 0.05 N aqueous ammonia and 0.3 N aqueous ammonia. Fractions containing the desired product were collected and lyophilized to give 804 mg of 3-O:4-N-carbonyl-5-de-O-methyl-KA-6606 II as a colorless powder.

Elemental analysis for $C_{15}H_{28}N_4O_5.2H_2O$:

| | C | H | N |
|---|---|---|---|
| Calculated (%) | 47.36 | 8.48 | 14.73 |
| Found (%) | 46.98 | 8.35 | 14.55 |

Specific rotation: $[\alpha]_D^{23}+86°$ (c 1, $H_2O$)

'H-NMR ($\delta_{D2O}$, ppm(TMS external standard)): 1.53 (3H, d, J=6.7 Hz, C—$\underline{CH_3}$), 3.52 (3H, s, N—$\underline{CH_3}$), 5.55 (1H, d, J=3.5 Hz, H-1').

(B) 260 mg of the above free base was dissolved in 2.5 ml of methanol, and 2.5 ml of a methanol solution (10% V/V) of anisaldehyde was added. The mixture was warmed at 37° C. for 2 hours. The reaction mixture was concentrated to dryness, and the residue was dissolved in toluene and again concentrated to dryness. The residue was dissolved in 10 ml of anhydrous dimethylformamide, and 550 mg of (S)-2,3-epoxypropyl-o-nitrobenzenesulfonate was added. In a stream of nitrogen, 150 mg of 50% oily sodium hydride was added, and the mixture was stirred at 0° to 5° C. for 3 hours. Water (7 ml) was added to the reaction mixture, and then 600 mg of concentrated sulfuric acid was added. The mixture was left to stand overnight at room temperature. Water (200 ml) was added to the reaction mixture, and the mixture was washed with three 100 ml portions of chloroform. The aqueous layer was charged onto a column filled with 20 ml of CM-Sephadex C-25 ($NH_4^+$ form). The column was washed with water, and then eluted with 0.6 N aqueous ammonia. The eluate was concentrated to dryness. The residue was dissolved in 13 ml of methanol, and 0.25 ml of triethylamine and 670 mg of N-(benzyloxycarbonyloxy)succinimide were added. The mixture was left to stand overnight at room temperature. The reaction mixture was concentrated to dryness. The residue was dissolved in chloroform, washed with water, dried, and concentrated to dryness. The residue was charged onto a column filled with 35 g of silica gel, and the column was developed with chloroform/methanol (20/1). Fractions containing the desired product were concentrated to give 120 mg of 1,2',6'-tris-N-benzyloxycarbonyl-3-O:4-N-carbonyl-5-de-O-methyl-5-O-[(S)-2,3-dihydroxypropyl]-KA-6606 II as a colorless solid.

Elemental analysis for $C_{42}H_{52}N_4O_{13}$:

| | C | H | N |
|---|---|---|---|
| Calculated (%) | 61.45 | 6.39 | 6.83 |
| Found (%) | 61.29 | 6.21 | 6.54 |

Specific rotation: $[\alpha]_D^{25}+34°$ (c 1, $CHCl_3$) $[\alpha]_D^{25}+56°$ (c 1, $CH_3OH$)

IR ($\nu_{max}^{CHCl_3}$, $cm^{-1}$): 1760 (cyclic carbamate).

'H-NMR ($\delta_{CDCl_3}^{TMS}$, ppm):

1.08 (3H, d, J=6.5 Hz, C—$C\underline{H}_3$). 2.87 (3H, s, N—$C\underline{H}_3$).

(C) 195 mg of the above 5-O-alkyl compound was dissolved in 6 ml of anhydrous pyridine. The solution was cooled to −20° C., and 130 mg of tosyl chloride was added. The mixture was left to stand overnight at the same temperature. Water (0.1 ml) was added to the reaction mixture, and under ice cooling, the mixture was allowed to stand for 1 hour, and then concentrated to dryness. The residue was dissolved in chloroform, washed successively with 0.4 N potassium hydrogen sulfate, a saturated aqueous solution of sodium hydrogen carbonate and water, and dried to evaporate the solvent. The residue was charged onto a column of silica gel, and the column was developed with chloroform/methanol (70/1) to give 135 mg of 1,2',6'-tris-N-benzyloxycarbonyl-3-O:4-N-carbonyl-5-de-O-methyl-5-O-[(R)-2-hydroxy-3-tosyloxypropyl]-KA-6606 II as a colorless solid.

Elemental analysis for $C_{49}H_{58}N_4O_{15}S$:

| | C | H | N | S |
|---|---|---|---|---|
| Calculated (%) | 60.36 | 6.00 | 5.75 | 3.29 |
| Found (%) | 60.12 | 5.88 | 5.72 | 3.04 |

Specific rotation: $[\alpha]_D^{25}+48°$ (c 0.5, $CH_3OH$)

IR ($\nu_{max}^{CHCl_3}$, $cm^{-1}$): 1760 (cyclic carbamate), 1175 ($SO_2$)

'H—NMR ($\delta_{CDCl_3}^{TMS}$, ppm):

1.11 (3H, d, J = 6.5Hz, C—$C\underline{H}_3$), 2.50 (3H, s, 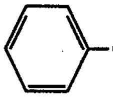 —$C\underline{H}_3$), 2.86 (3H, s, N—$C\underline{H}_3$).

(D) 100 mg of the tosyl compound obtained in (C) was dissolved in 3 ml of dimethylformamide, and 200 mg of sodium azide was added. The mixture was stirred at 60° C. for 7 hours. After the reaction, 30 ml of chloroform was added. The mixture was washed with three 30 ml portions of water, and then dried to evaporate the solvent. The residue was dissolved in toluene, and again concentrated to dryness to give 85 mg of 5-O-[(S)-3-azido-2-hydroxypropyl]-1,2',6'-tris-N-benzyloxycarbonyl-3-O:4-N-carbonyl-5-de-O-methyl-KA-6606 II as a colorless solid.

Elemental analysis for $C_{42}H_{51}N_7O_{12}$:

| | C | H | N |
|---|---|---|---|
| Calculated (%) | 59.63 | 6.08 | 11.59 |
| Found (%) | 59.45 | 5.92 | 11.71 |

Specific rotation: $[\alpha]_D^{25}+41°$ (c 1, $CHCl_3$) $[\alpha]_D^{25}+55°$ (c 1, $CH_3OH$)

IR ($\nu_{max}^{CHCl_3}$, $cm^{-1}$): 2095 (azide), 1760 (cyclic carbamate)

'H-NMR ($\delta_{CDCl_3}^{TMS}$, ppm): 1.09 (3H, d, J=6.5 Hz, C—$C\underline{H}_3$), 2.88 (3H, s, N—$C\underline{H}_3$).

(E) 55 mg of the azide compound obtained in (D) was dissolved in 1.1 ml of dioxane, and 1.1 ml of water, and 90 mg of barium hydroxide octahydrate were added. The mixture was stirred at 60° C. for 12 hours. The reaction mixture was neutralized with carbon dioxide gas. The insoluble materials were removed by filtration, and the filtrate was concentrated under reduced pressure.

The residue was dissolved in 3 ml of dioxane, and 0.1 ml of triethylamine and 80 mg of N-hydroxysuccinimide ester of N-benzyloxycarbonylglycine were added. The mixture was stirred at 60° C. for 5 hours. To the reaction mixture was added 0.3 ml of concentrated aqueous ammonia, and the mixture was left to stand at room temperature for 1 hour, and then concentrated to dryness. The residue was dissolved in chloroform, washed with water, dried, and then charged onto a column of silica gel. The column was developed with benzene/ethyl acetate (4/3). Fractions containing the desired product were concentrated and further purified by preparative thin-layer chromatography [plate: Silicagel $PF_{254}$ (Merck & Co.); developing solvent: chloroform/acetone (2/1)] to give 20 mg of 5-O-[(S)-3-azido-2-hydroxypropyl]-1,2',6'-tris-N-benzyloxycarbonyl-4-N-(N-benzyloxycarbonylglycyl)-5-de-O-methyl-KA-6606 II as a colorless solid.

Elemental analysis for $C_{51}H_{62}N_8O_{14}$:

| | C | H | N |
|---|---|---|---|
| Calculated (%) | 60.58 | 6.18 | 11.08 |
| Found (%) | 60.53 | 6.04 | 10.77 |

Specific rotation: $[\alpha]_D^{24}+35°$ (c 1, $CHCl_3$)

$[\alpha]_D^{24}+40°$ (c 1, benzene $[\alpha]_D^{24}+45°$ (c 1, $CH_3OH$)

IR ($\nu_{max}^{CHCl_3}$, $cm^{-1}$): 2100 (azide). 'H-NMR ($\delta_{CDCl_3}^{TMS}$, ppm): 1.08 (3H, d, J=7 Hz, C—$C\underline{H}_3$), 2.92 (3H, s, N—$C\underline{H}_3$).

(F) 20 mg of the 4-N-protected glycyl compound obtained in (E) was dissolved in 0.5 ml of acetic acid, and 20 mg of 5% palladium carbon was added. Thus, the above compound was catalytically reduced at room temperature and atmospheric pressure. After the reaction, the catalyst was removed by filtration. The filtrate was diluted with water to a volume of 50 ml, neutralized with aqueous ammonia, and charged onto a column of CM-Sephadex C-25 ($NH_4^+$ form). The column was eluted by a concentration gradient method using 0.05 N aqueous ammonia and 0.5 N aqueous ammonia. Fractions containing the desired product was lyophilized to give 5 mg of 5-O-[(S)-3-amino-2-hydroxypropyl]-5-de-O-methyl-KA-6606 I having the following structural formula as a colorless solid.

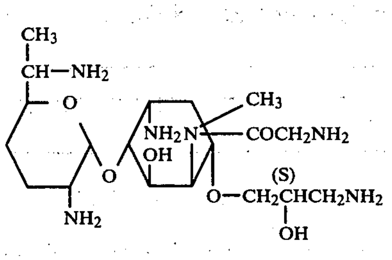

Elemental analysis for $C_{19}H_{40}N_6O_6.H_2CO_3$:

| | C | H | N |
|---|---|---|---|
| Calculated (%) | 47.05 | 8.29 | 16.46 |
| Found (%) | 46.89 | 8.03 | 16.44 |

Specific rotation: $[\alpha]_D^{22}+101°$ (c 0.2, $H_2O$)

IR ($\nu_{max}^{KBr}$, $cm^{-1}$): 1630 (amide I), 1580 (amide II).

'H-NMR ($\delta_{D_2O}$, ppm, (TMS external standard)): 1.54 (3H, d, J=6.5 Hz, C—$C\underline{H}_3$), 3.55 (3H, s, N—$C\underline{H}_3$), 5.45 (1H, d, J=3.5 Hz, H-1').

EXAMPLE 17

Production of 5-O-[(R)-3-amino-2-hydroxypropyl]-5-de-O-methyl-KA-6606 I:

(A) 950 mg of 3-O:4-N-carbonyl-5-de-O-methyl-KA-6606 II obtained in Example 16, (A) was reacted and treated in the same way as in Example 16, (B) except that (R)-2,3-epoxypropyl O-nitrobenzenesulfonate was used instead of (S)-2,3-epoxypropyl o-nitrobenzenesulfonate. There was obtained 324 mg of 1,2',6'-tris-N-benzyloxycarbonyl-3-O:4-N-carbonyl-5-de-O-methyl-5-O-[(R)-2,3-dihydroxypropyl]-KA-6606 II as a colorless solid.

Elemental analysis for $C_{42}H_{52}N_4O_{13}$:

| | C | H | N |
|---|---|---|---|
| Calculated (%) | 61.45 | 6.39 | 6.83 |
| Found (%) | 61.31 | 6.42 | 6.67 |

Specific rotation: $[\alpha]_D^{25}+36°$ (c 1, $CHCl_3$) $[\alpha]_D^{25}+55°$ (c 1, $CH_3OH$)

IR ($\nu_{max}^{CHCl_3}$, $cm^{-1}$): 1763 (cyclic carbamate)

'H-NMR ($\delta_{CDCl_3}^{TMS}$, ppm): 1.08 (3H, d, J=6.5 Hz, C—$C\underline{H}_3$), 2.88 (3H, s, N—$C\underline{H}_3$).

(B) 324 mg of the 5-O-alkyl compound obtained in (A) was reacted and treated in the same way as in Example 16, (C) to give 299 mg of 1,2',6'-tris-N-benzyloxycarbonyl-3-O:4-N-carbonyl-5-de-O-methyl-5-O-[(S)-2-hydroxy-3-tosyloxypropyl]-KA-6606 II as a colorless solid.

Elemental analysis for $C_{49}H_{58}N_4O_{15}S$:

| | C | H | N | S |
|---|---|---|---|---|
| Calculated (%) | 60.36 | 6.00 | 5.75 | 3.29 |
| Found (%) | 60.17 | 5.85 | 5.93 | 3.11 |

Specific rotation: $[\alpha]_D^{21}+52°$ (c 0.88, $CH_3OH$)

IR ($\nu_{max}^{CHCl_3}$, $cm^{-1}$): 1765 (cyclic carbamate), 1175 ($SO_2$).

'H—NMR($\delta_{CDCl_3}^{TMS}$, ppm):

1.09 (3H, d, J = 6.5 HZ, C—$C\underline{H}_3$), 2.49 (3H, s, 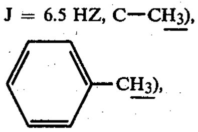), 2.86 (3H, s, N—$C\underline{H}_3$).

(C) 317 mg of the tosyl compound obtained in (B) was reacted and treated in the same way as in Example 16, (D) to give 251 mg of 5-O-[(R)-3-azido-2-hydroxypropyl]-1,2',6'-tris-N-benzyloxycarbonyl-3-O:4-N-carbonyl-5-de-O-methyl-KA-6606 II as a colorless solid.

Elemental analysis for $C_{42}H_{51}N_7O_{12}$.

| | C | H | N |
|---|---|---|---|
| Calculated (%) | 59.63 | 6.08 | 11.59 |
| Found (%) | 59.32 | 6.27 | 11.54 |

Specific rotation: $[\alpha]_D^{22}+39°$ (c 1, $CHCl_3$)

$[\alpha]_D^{22}+60°$ (c 1, $CH_3OH$)

IR ($\nu_{max}^{CHCl_3}$, $cm^{-1}$): 2100 (azide), 1765 (cyclic carbamate).

'H-NMR ($\delta_{CDCl_3}^{TMS}$, ppm): 1.08 (3H, d, J=6.5 Hz, C—$C\underline{H}_3$), 2.87 (3H, s, N—$C\underline{H}_3$).

(D) 250 mg of the azido compound obtained in (C) was reacted and treated in the same way as in Example 16, (E) to give 121 mg of 5-O-[(R)-3-azido-2-hydroxypropyl]-1,2',6'-tris-N-benzyloxycarbonyl-4-N-(N-benzyloxycarbonylglycyl)-5-de-O-methyl-KA-6606 II as a colorless solid.

Elemental analysis for $C_{51}H_{62}N_8O_{14}$:

| | C | H | N |
|---|---|---|---|
| Calculated (%) | 60.58 | 6.18 | 11.08 |
| Found (%) | 60.34 | 6.29 | 10.88 |

Specific rotation: $[\alpha]_D^{22}+37°$ (c 1, $CHCl_3$), $[\alpha]_D^{22}+38°$ (c 1, benzene), $[\alpha]_D^{22}+51°$ (c 1, $CH_3OH$).

IR ($\nu_{max}^{CHCl_3}$, $cm^{-1}$): 2095 (azide)

'H-NMR ($\delta_{CDCl_3}^{TMS}$, ppm): 1.07 (3H, d, J=7 Hz, C—$C\underline{H}_3$), 2.91 (3H, s, N—$C\underline{H}_3$).

(E) 121 mg of the 4-N-protected glycyl compound obtained in (D) was reacted and treated in the same way as in Example 16, (F) to give 33 mg of 5-O-[(R)-3-amino-2-hydroxypropyl]-5-de-O-methyl-KA-6606 I as a colorless solid having the following structural formula.

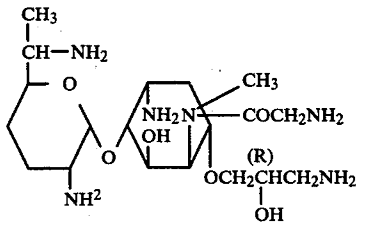

Elemental analysis for $C_{19}H_{40}N_6O_6.H_2CO_3$:

| | C | H | N |
|---|---|---|---|
| Calculated (%) | 47.05 | 8.29 | 16.46 |
| Found (%) | 46.90 | 8.22 | 16.27 |

Specific rotation: $[\alpha]_D^{22}+114°$ (c 1, $H_2O$)

IR ($\nu_{max}^{KBr}$, $cm^{-1}$): 1628 (amide I), 1575 (amide II).

'H-NMR ($\delta_{D_2O}$, ppm (TMS external standard): 1.53 (3H, d, J=6.5 Hz, C—$CH_3$), 3.55 (3H, s, N—$CH_3$), 5.45 (1H, d, J=3.5 Hz, H-1').

Referential Example

Production of (R) or (S)-2,3-epoxypropyl o-nitrobenzenesulfonate used in Examples 16 and 17:

One gram of (R) or (S)-glycidol was dissolved in 20 ml of anhydrous toluene, and 2 ml of triethylamine was added. The mixture was cooled with ice, and 2.79 g of o-nitrobenzenesulfonyl chloride was added with stirring in three portions at an interval of 10 minutes. The mixture was further stirred for 1 hour with ice cooling. After the reaction, the insoluble materials were removed by filtration. The filtrate was concentrated at below 30° C., and the residue was charged onto a column of silica gel. The column was developed with benzene/ethyl acetate (10/1) to give 1.9 g of (S)-compound from (R)-glycidol, and 2.54 g of (R)-compound from (S)-glycidol.

The (S)- and (R)-compounds were colorless syrupy substances of the following formulae.

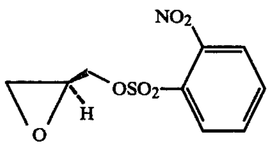

(S)-compound

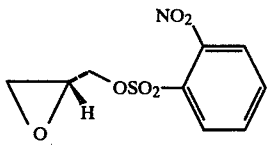

(R)-compound

Specific rotation:

(S)-compound: $[\alpha]_D^{24}+4°$ (c 3, $CHCl_3$), $[\alpha]_D^{24}+14°$ (c 3, benzene), (R)-compound: $[\alpha]_D^{24}-13.3°$ (c 4, benzene).

'H-NMR ($\delta_{CDCl_3}^{TMS}$, ppm): 4.61 (1H, dd, J=3.5, 12 Hz), 4.20 (1H, dd, J=6, 12 Hz), 3.3 (1H, m), 2.88 (1H, t, J=4.5 Hz), 2.71 (1H, dd, J=2.5, 4.5 Hz).

What we claim is:

1. A compound of the following formula

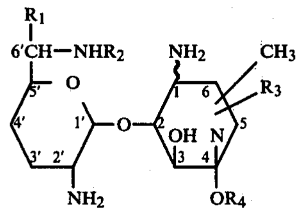

(I)

wherein one of $R_1$ and $R_2$ represents a hydrogen atom and the other, a methyl group, $R_3$ represents a hydrogen atom or an amino acyl group having 2 to 5 carbon atoms, $R_4$ represents a lower alkyl group substituted by one or two substituents selected from the class consisting of hydroxy and amino groups, or a hexopyranosyl group whose hydroxy groups may be substituted by amino groups, or a pharmaceutically acceptable acid addition salt thereof.

2. The compounds of claim 1 wherein $R_4$ is a $C_2$-$C_6$ alkyl group substituted by one of two substituents selected from the class consisting of hydroxy and amino groups, a glucopyranosyl group, or a glycopyranosyl group having an amino group at the 3-position.

3. An antibiotic composition consisting essentially of (i) an antibiotically effective amount of a compound of the following formula

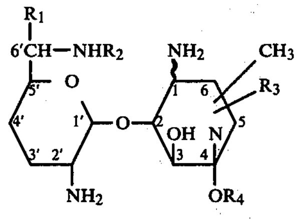

(I)

wherein one of $R_1$ and $R_2$ represents a hydrogen atom and the other, a methyl group, $R_3$ represents a hydrogen atom or an amino acyl group having 2 to 5 carbon atoms, $R_4$ represents a lower alkyl group substituted by one or two substituents selected from the class consisting of hydroxy and amino groups, or a hexopyranosyl group whose hydroxy groups may be substituted by amino groups, or a pharmaceutically acceptable acid addition salt thereof, and (ii) a pharmaceutically acceptable diluent or carrier.

4. The composition of claim 3 wherein the amount of the compound of formula (I) or its pharmaceutically acceptable acid addition salt is about 0.01 to 99.5% by weight based on the composition.

* * * * *